US012693441B2

(12) United States Patent
Lyu et al.

(10) Patent No.: US 12,693,441 B2
(45) Date of Patent: Jul. 28, 2026

(54) SYSTEM AND METHOD FOR CALIBRATING A PET SCANNER

(71) Applicant: SHANGHAI UNITED IMAGING HEALTHCARE CO., LTD., Shanghai (CN)

(72) Inventors: Xinyu Lyu, Shanghai (CN); Qixiang Zhang, Shanghai (CN); Wenbing Song, Shanghai (CN); Zijun Ji, Shanghai (CN); Weiping Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 703 days.

(21) Appl. No.: 18/295,239

(22) Filed: Apr. 3, 2023

(65) Prior Publication Data

US 2023/0243988 A1 Aug. 3, 2023

Related U.S. Application Data

(63) Continuation-in-part of application No. 16/882,556, filed on May 25, 2020, now Pat. No. 11,619,755, (Continued)

(30) Foreign Application Priority Data

| | | |
|---|---|---|
| Sep. 21, 2015 | (CN) | 201510603207.2 |
| Nov. 28, 2015 | (CN) | 201510854615.5 |

(Continued)

(51) Int. Cl.
| | |
|---|---|
| *G01T 7/00* | (2006.01) |
| *A61B 6/03* | (2006.01) |

(Continued)

(52) U.S. Cl.
CPC .............. *G01T 7/005* (2013.01); *A61B 6/037* (2013.01); *A61B 6/583* (2013.01);
(Continued)

(58) Field of Classification Search
CPC . G01T 7/005; G01T 1/2985; G01N 2201/121; A61B 6/037; A61B 6/583
See application file for complete search history.

(56) References Cited

U.S. PATENT DOCUMENTS

| | | | | |
|---|---|---|---|---|
| 5,272,343 A | * | 12/1993 | Stearns | ................... G01T 1/172 |
| | | | | 250/363.04 |
| 7,201,515 B2 | | 4/2007 | Lacey | |

(Continued)

FOREIGN PATENT DOCUMENTS

| | | |
|---|---|---|
| CN | 101297758 A | 11/2008 |
| CN | 102755172 A | 10/2012 |

(Continued)

OTHER PUBLICATIONS

International Search Report in PCT/CN2016/099078 mailed on Nov. 29, 2016, 5 pages.

(Continued)

*Primary Examiner* — Carolyn Fin
(74) *Attorney, Agent, or Firm* — METIS IP LLC

(57) ABSTRACT

A method and system for calibrating a PET scanner are described. The PET scanner may have a field of view (FOV) and multiple detector rings. A detector ring may have multiple detector units. A line of response (LOR) connecting a first detector unit and a second detector unit of the PET scanner may be determined. The LOR may correlate to coincidence events resulting from annihilation of positrons emitted by a radiation source. A first time of flight (TOF) of the LOR may be calculated based on the coincidence events. The position of the radiation source may be determined. A (Continued)

coincident event detection circuit

100 second TOF of the LOR may be calculated based on the position of the radiation source. A time offset may be calculated based on the first TOF and the second TOF. The first detector unit and the second detector unit may be calibrated based on the time offset.

20 Claims, 29 Drawing Sheets

Related U.S. Application Data which is a continuation of application No. 15/171, 877, filed on Jun. 2, 2016, now Pat. No. 10,663,608.

(30) Foreign Application Priority Data

| | | | |
|---|---|---|---|
| Dec. 31, 2015 | (CN) | ......................... | 201511031899.4 |
| Dec. 31, 2015 | (CN) | ......................... | 201521140680.3 |

(51) Int. Cl.
| | |
|---|---|
| *A61B 6/58* | (2024.01) |
| *G01N 23/2206* | (2018.01) |
| *G01T 1/29* | (2006.01) |

(52) U.S. Cl.
CPC ....... *G01N 23/2206* (2013.01); *G01T 1/2985* (2013.01); *G01N 2223/071* (2013.01); *G01N 2223/303* (2013.01); *G01N 2223/304* (2013.01)

(56) References Cited

U.S. PATENT DOCUMENTS

| | | | |
|---|---|---|---|
| 7,887,237 B2 | 2/2011 | Krug |
| 8,455,834 B2 | 6/2013 | Tsukerman |
| 8,796,637 B1 | 8/2014 | Burr et al. |
| 2003/0212320 A1 | 11/2003 | Wilk et al. |
| 2004/0202287 A1 | 10/2004 | Muller |
| 2007/0080296 A1 | 4/2007 | Ueno et al. |
| 2007/0131857 A1 | 6/2007 | Thompson et al. |
| 2007/0152162 A1 | 7/2007 | Griesmer et al. |
| 2007/0205368 A1 | 9/2007 | Heukensfeldt Jansen et al. |
| 2007/0278409 A1* | 12/2007 | Cook ..................... G01T 1/2985 250/363.03 |
| 2008/0265167 A1* | 10/2008 | Laurence .............. G01T 1/2985 250/363.09 |
| 2010/0020209 A1 | 1/2010 | Kim |
| 2010/0266096 A1 | 10/2010 | Sharpless |
| 2011/0127413 A1 | 6/2011 | Casey et al. |
| 2011/0309252 A1 | 12/2011 | Moriyasu et al. |
| 2013/0123602 A1 | 5/2013 | Kovalski et al. |
| 2014/0142892 A1 | 5/2014 | Song et al. |

FOREIGN PATENT DOCUMENTS

| | | |
|---|---|---|
| CN | 104434160 A | 3/2015 |
| CN | 104644204 A | 5/2015 |
| CN | 105193441 A | 12/2015 |
| CN | 105411618 A | 3/2016 |
| CN | 105496436 A | 4/2016 |
| JP | 2012021976 A | 2/2012 |
| JP | 5672061 B2 | 2/2015 |
| WO | 2015028602 A1 | 3/2015 |

OTHER PUBLICATIONS

Written Opinion in PCT/CN2016/099078 mailed on Nov. 29, 2016, 5 pages.
First Office Action in Chinese Application No. 201510854615.5 mailed on Apr. 25, 2017, 11 pages.
First Office Action in Chinese Application No. 201511031899.4 mailed on Dec. 21, 2017, 13 pages.
First Office Action in Chinese Application No. 201510603207.2 mailed on Jul. 1, 2019, 13 pages.
The Extended European Search Report in European Application No. 16848062.2 mailed on Sep. 3, 2018, 7 pages.
Notice of Reasons for Rejection in Japanese Application No. 2018514820 mailed on Aug. 4, 2020, 10 pages.
Li, Hongdi et al., An Accurate Timing Alignment Method With Time-to-Digital Converter Linearity Calibration for High-Resolution TOF PET, IEEE Transactions on Nuclear Science, 62(3): 799-804, 2015.
Decision of Patent Grant in Korean Application No. 10-2018-7010475 mailed on Jul. 2, 2024, 9 pages.

\* cited by examiner

400

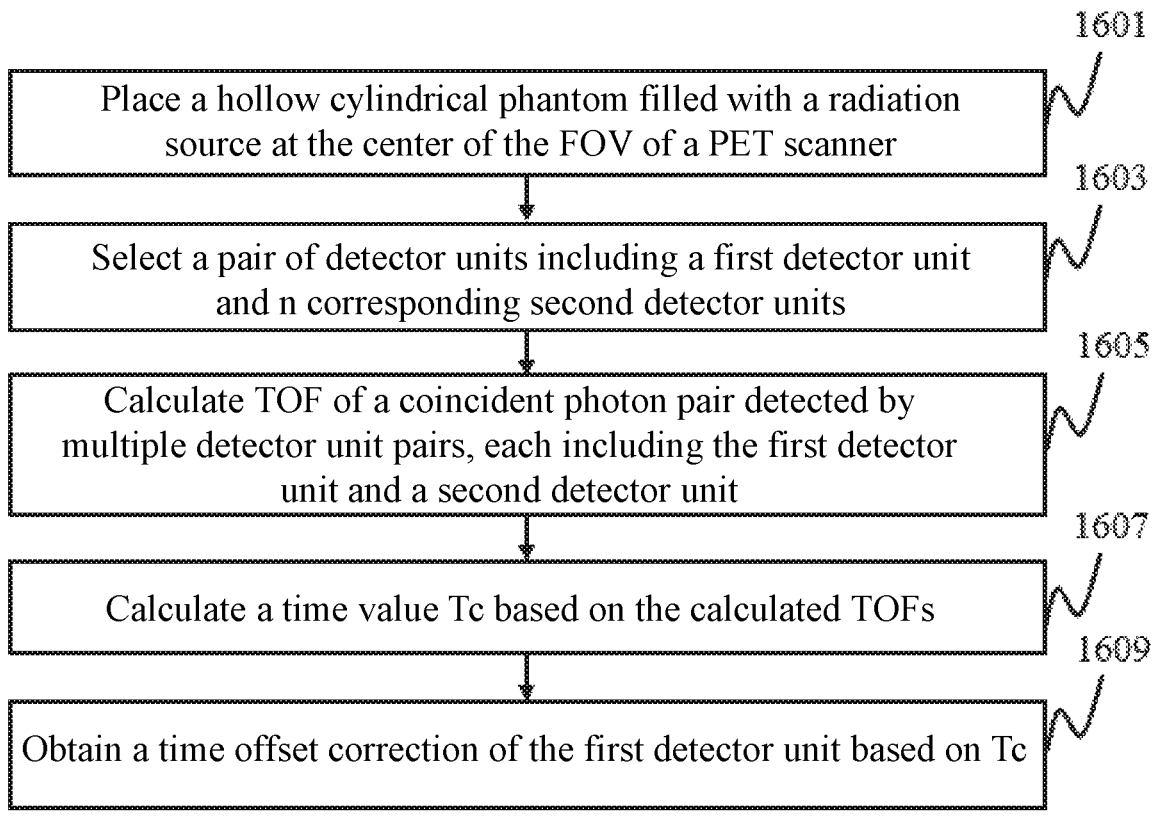

1601

Place a hollow cylindrical phantom filled with a radiation source at the center of the FOV of a PET scanner

1603

Select a pair of detector units including a first detector unit and n corresponding second detector units

1605

Calculate TOF of a coincident photon pair detected by multiple detector unit pairs, each including the first detector unit and a second detector unit

1607

Calculate a time value Tc based on the calculated TOFs

1609

Obtain a time offset correction of the first detector unit based on Tc

FIG. 16

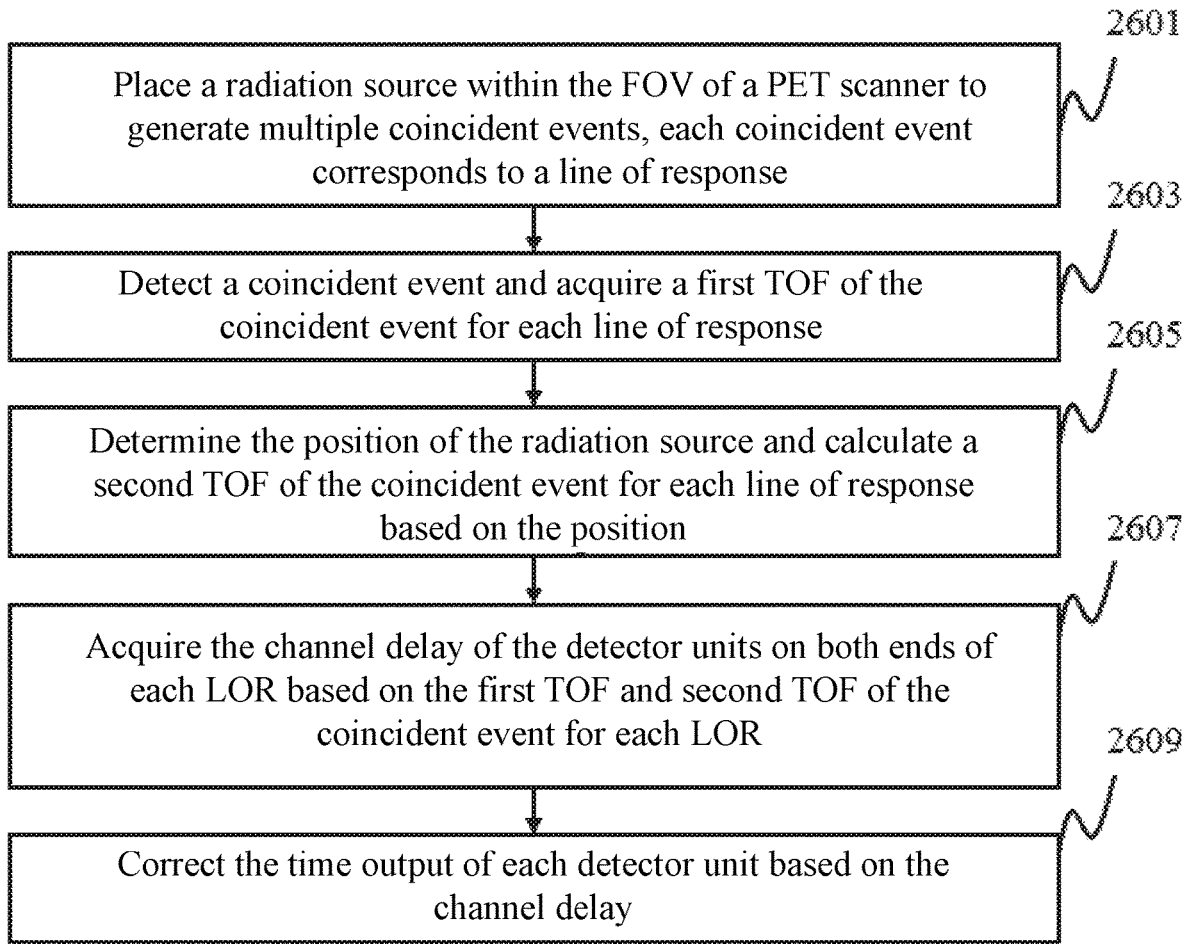

2601

Place a radiation source within the FOV of a PET scanner to generate multiple coincident events, each coincident event corresponds to a line of response

2603

Detect a coincident event and acquire a first TOF of the coincident event for each line of response

2605

Determine the position of the radiation source and calculate a second TOF of the coincident event for each line of response based on the position

2607

Acquire the channel delay of the detector units on both ends of each LOR based on the first TOF and second TOF of the coincident event for each LOR

2609

Correct the time output of each detector unit based on the channel delay

FIG. 26

SYSTEM AND METHOD FOR CALIBRATING A PET SCANNER

CROSS REFERENCE TO RELATED APPLICATIONS

This application is a Continuation-in-part of U.S. application Ser. No. 16/882,556, filed on May 25, 2020, which is a Continuation of U.S. application Ser. No. 15/171,877 (now U.S. Pat. No. 10,663,608), filed on Jun. 2, 2016, which claims priority of Chinese Patent Application No. 201510603207.2 filed on Sep. 21, 2015, Chinese Patent Application No. 201510854615.5 filed on Nov. 28, 2015, Chinese Patent Application No. 201511031899.4 filed on Dec. 31, 2015, and Chinese Patent Application No. 201521140680.3 filed on Dec. 31, 2015, each of which is hereby incorporated by reference.

TECHNICAL FIELD

The present disclosure generally relates to imaging, and more particularly, a system and method for TOF calibration in a PET scanner.

BACKGROUND

Positron emission tomography (PET) has been widely used in medicine for diagnosis and other purposes. A subject, such as a patient, may be scanned with a PET scanner to obtain medical images. A PET scanner includes a plurality of detector units. The detector units are used for detecting coincidence events.

Time-of-flight (TOF) information is generally used for PET image reconstruction. For an annihilation event, the time that each of the coincident photons is detected at two detector units (or referred to as arrival time), and the difference is calculated. Since the travel distances of the two photons to their respective detector units may be different from each other, the photon whose travel distance is shorter may arrive at its detector unit first, compared to the other photon. The difference in the arrival time of the coincident photons may help pin down the location of the annihilation event along the line between the two detector units. Accurate TOF may allow the reconstruction of a PET image.

In general, a phantom is used to calibrate and/or verify the accuracy of a PET scanner. A phantom is a model with a known geometry (e.g., shape, size, etc.) and/or a known distribution of radiation activities throughout the body of the phantom. By imaging the phantom, the accuracy of the imaging apparatus for a three-dimensional or two-dimensional image may be assessed and the settings of the PET scanner may be adjusted based on the phantom data. For instance, the time offset of a detector unit may be calibrated. A phantom may be designed to be a solid body, and the phantom may be placed at the center of the FOV of the PET scanner for a calibration scan. Thus, a device to adjust the position of the phantom is needed. Furthermore, these requests make the phantom imaging process complicated and time-consuming. A method to determine the time offset for detector units is described in this application.

SUMMARY

In a first aspect of the present disclosure, a method for calibrating a PET scanner is provided. The PET scanner has a field of view (FOV) and a plurality of detector rings. Each detector ring has a plurality of detector units. Each detector unit may have a plurality of crystal elements. The method may determining a line of response (LOR) correlating to a plurality of coincidence events. The LOR connects a first detector unit and a second detector unit of the PET scanner. The method may also include calculating a first time of flight (TOF) of the LOR based on the plurality of coincidence events. The method may further include determining the position of the radiation source and calculating a second TOF of the LOR based on the position of the radiation source. The method may include calculating a time offset based on the first TOF and the second TOF, and the first unit and the second unit may be calibrated based on the time offset. In some embodiments, the time offset may be due to a channel delay. In some embodiments, the first TOF may be calculated based on a filter window.

In a second aspect of the present disclosure, a PET scanner is provided. The PET scanner has a plurality of detector rings, and each detector ring has a plurality of detector units. The PET scanner may include a coincidence event detection circuit for detecting coincidence events resulting from annihilation of positrons emitted by a radiation source. The PET scanner may also include a host computer that is configured to determine an LOR connecting a first detector unit and a second detector unit of the plurality of detector units and the LOR may correlate to a plurality of coincidence events, calculate a first TOF of the LOR based on the plurality of coincidence events, determine the position of the radiation source, calculate a second TOF of the LOR based on the position of the radiation source, calculate a time offset based on the first TOF and the second TOF, and calibrate the first detector unit and the second detector unit based on the time offset.

In some embodiments, the position of the radiation source may be adjusted based on a target position. In some embodiments, the target position may include a target axial position and a target circumferential position. In some embodiments, the first TOF may be an average of each TOF of the plurality of coincidence events.

In some embodiments, the first TOF of the LOR may be calculated based on the plurality of coincidence events. In some embodiments, a histogram may be created based on TOFs of the plurality of coincidence events. The time value of the center of the histogram may be calculated. In some embodiments, a sinogram corresponding to the plurality of coincidence events may be created. A measurement TOF of the LOR may be calculated based on the sinogram. The first TOF may be assessed based on the measurement TOF.

In some embodiments, the second TOF may be calculated based on the position of the radiation source. An intersection portion of the LOR and the radiation source may be determined. A center of the intersection portion may be determined. The second TOF may be calculated based on the coincidence event occurred in the center of the intersection portion. In some embodiments, the radiation source may be wrapped by a phantom.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein:

FIG. 16 is a flowchart illustrating a process for time calibration according to some embodiments of the present disclosure;

FIG. 26 is a flowchart illustrating a process for time calibration according to some embodiments of the present disclosure.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

It will be understood that when a module or unit is referred to as being "on," "connected to," or "coupled to" another module or unit, it may be directly on, connected or coupled to the other module or unit or intervening module or unit may be present. In contrast, when a module or unit is referred to as being "directly on," "directly connected to" or "directly coupled to" another module or unit, there may be no intervening module or unit present. As used herein, the term "and/or" includes any and all combinations of one or more of the associated listed items.

The terminology used herein is for the purpose of describing particular example embodiments only and is not intended to be limiting. As used herein, the singular forms "a", "an" and "the" may be intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
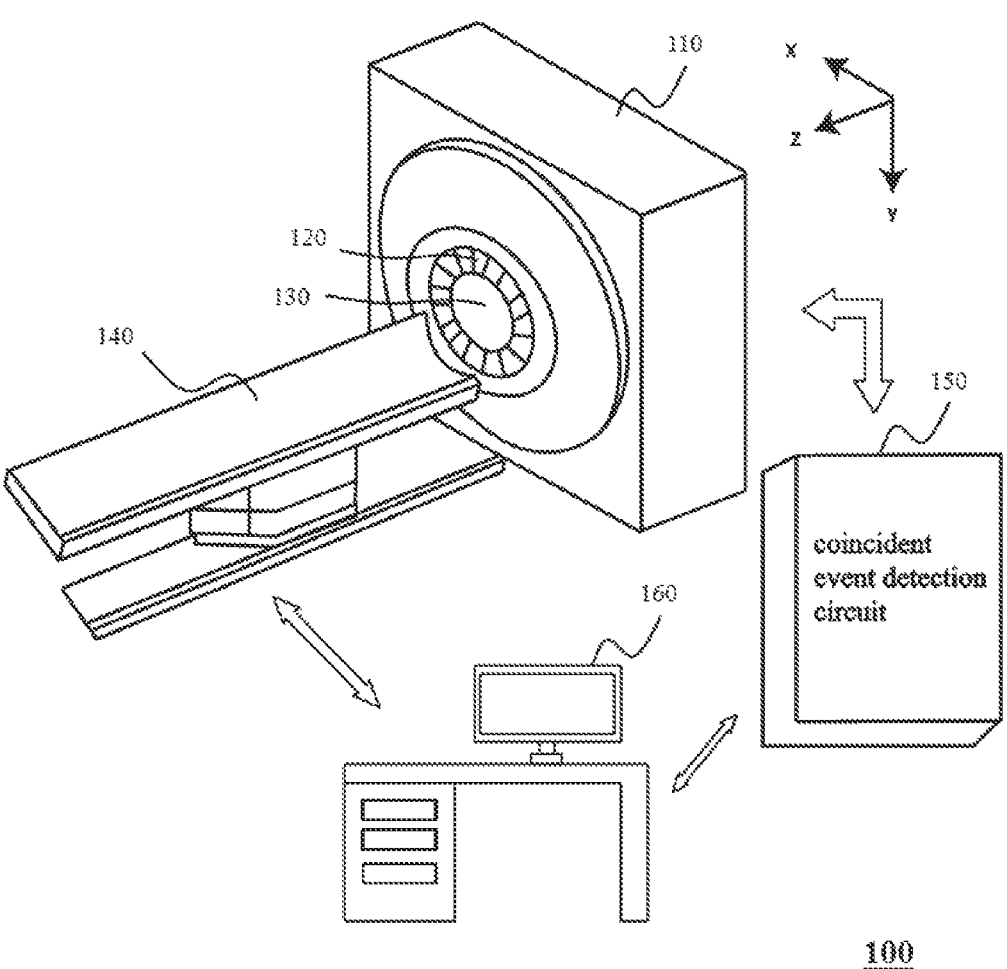
FIG. 1 illustrates an exemplary PET scanner according to some embodiments of the present disclosure.

FIG. 1 is an exemplary PET scanner 100 according to some embodiments of the present disclosure. The PET scanner 100 may include a scanning bore 110, a detector ring 120, a table 140, a coincidence event detection circuit 150, and a host computer 160.

In some embodiments, the scanning bore 110 may be configured to include the detector ring 120 and be connected with the coincidence event detection circuit 150. As shown in the figure, a coordinate system may be employed. The z-axis may denote the longitudinal axis of the scanning bore 110, and the plane defined by the x-axis and the y-axis, i.e., the x-y plane, may denote the cross section of the scanning bore 110 viewed along the longitudinal axis, (which is also referred to as the longitudinal section of the scanning bore 110). In some embodiments, the scanning bore 110 may include a plurality of detector rings, for example, 96 detector rings.

The detector ring 120 may include a plurality of detector units, the detector units may be implemented in any suitable manner, for example, a ring, a rectangle, an array, etc. The detector ring 120 may be arranged around a detecting region 103 to detect radiation events (e.g., gamma rays, coincidence events, photons, etc.) emitted from the detecting region 130. In some embodiments, the detector units of the detector ring 120 may be arranged in a number of detector rings (e.g., two, five, ten, a hundred, etc.) along an axial direction. In some embodiments, a detector unit of the detector ring 120 may include one or more crystal elements and/or one or more photomultiplier tubes (PMT) (not shown in the figure).

In some embodiments, a PMT as employed in the present disclosure may be a single-channel PMT. In some embodiments, a PMT as employed in the present disclosure may be a multi-channel PMT.

The table 140 may be configured to position a patient or a subject in the detecting region 130. In some embodiments, the table 140 may be linearly moved in an axial direction or the z-direction that is transverse to the detector ring 120 to facilitate the acquisition of three-dimensional (3D) data. In some embodiments, the table 140 may be used to adjust the position of a radiation source.

In some embodiments, a radiation source may be injected into a subject (e.g., a patient). The subject may be positioned in the detecting region 130. The radiation source placed in the subject may undergo radioactive decay, which may generate an emission of positrons. The positrons may interact with electrons nearby and start to annihilate. The annihilation may produce two oppositely directed gamma photons. The two oppositely directed gamma photons may strike the detector ring 120, e.g., the crystal element(s) of the detector ring 120. The crystal element(s) may produce a scintillation of light when struck by the gamma photons. The light produced by the crystal element(s) may be received by one or more PMTs. The PMTs may be configured to convert the light into one or more electrical signals. The coincidence event detection circuit 150 may be configured to receive the electrical signals and provide signal amplification, filtering, conditioning, etc.

The coincidence event detection circuit 150 may include a converter (not shown in the figure) that may be used to digitize and time stamp the electrical signals. The coincidence event detection circuit 150 may also include a pair detector (not shown in the figure) that may be used to detect and identify photon pair(s) belonging to a coincidence event. The term "photon pair" as used herein may refer to a pair of gamma photons that belong to a coincidence event resulting from a single annihilation. Upon identifying a photon pair, a line of response (LOR) processor (not shown in the figure) may process spatial information of the photon pair to identify an LOR connecting the two gamma photons. Since the two gamma photons emitted in an annihilation event are spatially oppositely directed, the annihilation event may be known to have occurred somewhere on the LOR. The detector ring 120 may have a sufficiently high temporal resolution to detect time-of-flight (TOF) between the two gamma photons belonging to a same coincidence event. A TOF processor (not shown in the figure) of the coincidence event detection circuit 150 may analyze the time difference between the arrival time of the two gamma photons to localize the position in which the annihilation event occurred along the LOR. The term "arrival time" as used herein may refer to the time a photon strikes a detector and/or a crystal element of the PET scanner. In some embodiments, a TOF may be calculated by the TOF processor. The term "TOF" as used herein may refer to the time difference between the arrival time of two gamma photons striking on the detector ring 120, and the two gamma photons belong to a same coincidence event.

As multiple coincidence events being accumulated in the PET scanner, a set of histoprojections may be generated. A reconstruction engine (not shown in the figure) of the coincidence event detection circuit 150 may be used to reconstruct the set of histoprojections to generate one or more images using a suitable reconstruction algorithm such as iterative backprojection with correction, filtered backprojection, etc. The raw data and/or the reconstructed images may be stored in a storage (not shown in the figure), and may be displayed, archived, processed, printed, filmed, transferred to another device, displayed on a display (not shown in the figure). A user including, for example, an operator, etc., may use the raw data and/or the reconstructed images to control the PET scanner 100, diagnose a subject, etc. In some embodiments, the user may control the PET scanner 100 via the host computer 160.

In some embodiments, the PET scanner may include a configuration engine. In some embodiments, the configuration engine may be used to calculate TOF. In some embodiments, the configuration engine may be used to calibrate TOF. In some embodiments, the configuration engine may be used to assess the quality of TOF. In some embodiment, the configuration engine may be used to adjustment the position of a radiation source. In some embodiments, the configuration engine may be located in the host computer 160. In some embodiments, the configuration engine may be part of the coincidence event detection circuit 150.

The LOR processor and/or the TOF processor may include any processor-based units and/or microprocessor-based units. Merely by way of example, the units may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. The exemplary types of processors that may be used in connection with the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

It should be noted that the description of the PET scanner is provided for the purposes of illustration, and not intended to limit the scope of the present disclosure. For persons having ordinary skills in the art, various modifications and variations may be conducted under the teaching of the present disclosure. However, those modifications and variations may still pertain to the present disclosure. For example, the PET scanner as described above may employ techniques including digital subtraction angiography (DSA), computed tomography (CT), computed tomography angiography (CTA), positron emission tomography (PET), X-ray imaging, magnetic resonance imaging (MRI), magnetic resonance angiography (MRA), single-photon emission computerized tomography (SPECT), ultrasound scanning (US), CT-MR, CT-PET, CE-SPECT, DSA-MR, PET-MR, PET-US, SPECT-US, transcranial magnetic stimulation (TMS)-MR, US-CT, US-MR, X-ray-CT, X-ray-MR, X-ray-portal, X-ray-US, Video-CT, and Vide-US. In some embodiments, the radiation source described above may include a phantom for testing the performance of the PET scanner.

Figure 2:
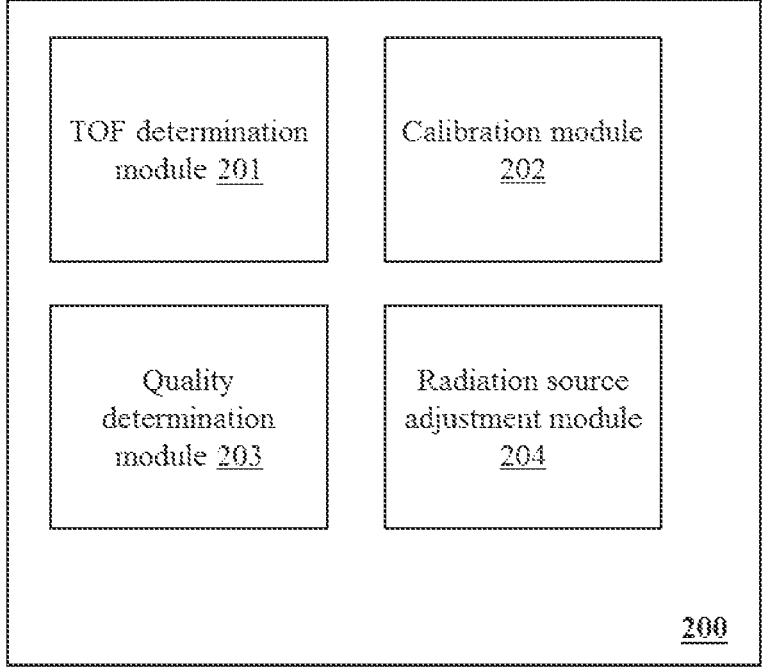
FIG. 2 is a block diagram of an exemplary configuration engine according to some embodiments of the present disclosure.

FIG. 2 is a block diagram of an exemplary configuration engine 200 implemented in the PET scanner 100 according to some embodiments of the present disclosure. As shown in the figure, the configuration engine 200 may include a TOF determination module 201, a calibration module 202, a quality determination module 203, and a radiation source adjustment module 204.

The TOF determination module 201 may be configured to calculate a TOF of a coincidence event. In some embodiments, the TOF determination module 201 may be used to calculate the TOF of an LOR.

The calibration module 202 may be configured to calibrate the PET scanner as described in connection with FIG. 1. In some embodiments, the calibration module 202 may be configured to calibrate the crystal elements of the PET scanner. In some embodiments, the calibration module 202 may be configured to calibrate the photomultiplier tubes of the PET scanner.

The quality determination module 203 may be configured to determine the quality of the TOF calculated by the TOF determination module 201. In some embodiments, the TOF calculated by the TOF determination module 201 may be assessed based on one or more measurement TOFs and/or thresholds.

The radiation source adjustment module 204 may be configured to adjust the position of a radiation source placed in the scanning region of the PET scanner. In some embodiments, the radiation source adjustment module 204 may be configured to adjust the position of a radiation source based on a target position.

It should be noted that the configuration engine described above is provided for the purposes of illustration, and not intended to limit the scope of the present disclosure. For persons having ordinary skills in the art, various modifications and variations may be conducted under the teachings of the present disclosure. However, those modifications and variations may not depart from the scope of the present disclosure.

Figure 3:
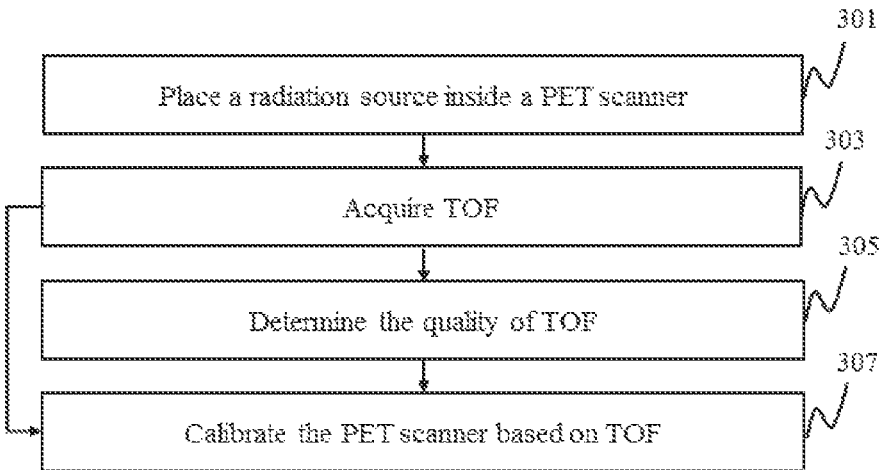
FIG. 3 is a flowchart illustrating a process for the calibration of a PET scanner according to some embodiments of the present disclosure.

FIG. 3 is a flowchart illustrating a process for TOF calibration according to some embodiments of the present disclosure.

In step 301, a radiation source may be placed in a PET scanner. In some embodiments, the radiation source may be placed in the scanning bore 110 of the PET scanner. In some embodiments, the radiation source may be placed in the center of the scanning bore 110. In some embodiments, the radiation source may be placed in the peripheral part of the center of the scanning bore 110.

In step 303, TOF may be acquired. In some embodiments, the TOF of a coincidence event may be acquired. In some embodiments, the TOF of an LOR may be acquired. In some embodiments, a plurality of coincidence events may correlate to the LOR, and each coincidence event may have an LOR. The TOF of the LOR may be calculated based on the plurality of LORs of the plurality of coincidence events. For example, the TOF of the LOR may be an average of the plurality TOFs. In some embodiments, a histogram may be created based on the plurality of TOFs, the TOF of the LOR may be calculated based on the histogram.

In step 305, the quality of TOF may be determine. In some embodiments, the TOF acquired in step 303 may be assessed in step 305. A TOF may be discarded if the assessment reveals that the TOF is unsatisfactory (or referred to as "succeed"), and the TOF may be validated if the assessment reveals that the TOF is satisfactory (or referred as to "fail").

In some embodiments, a measurement TOF may be calculated, and the assessment of the TOF may be based on the measurement TOF.

In step 307, the PET scanner may be calibrated based on TOF. In some embodiments, a time offset table may be prestored in or accessible from the PET scanner. TOF calculated by the PET scanner may be calibrated based on the time offset table.

It should be noted that the flowchart is provided for the purposes of illustration, and not intended to limit the scope of the present disclosure. In some embodiments, step 305 may be skipped, and step 303 may proceed to step 307 directly.

Figure 4:
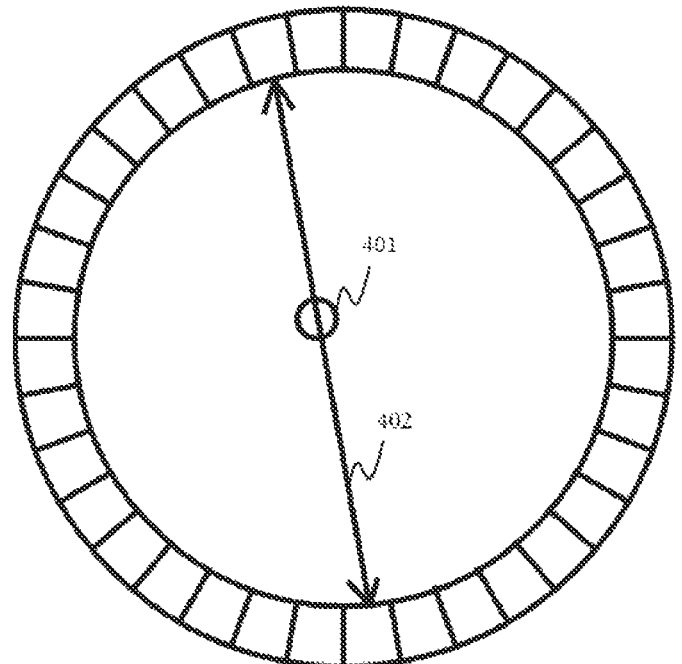
FIG. 4 illustrates an exemplary detector ring according to some embodiments of the present disclosure.

FIG. 4 illustrates an exemplary detector ring 400 according to some embodiments of the present disclosure. As shown in the figure, the detector ring 400 may include a plurality of detector units arranged in a ring. A radiation source 401 may be placed in the detector ring 400. The radiation source 401 may decay and generate an emission of positrons. The positrons may interact with electrons nearby and annihilation may occur. The annihilation may produce two gamma photons that may strike the detector ring 400, e.g., one or more detector units of the detector ring 400. A spatial line indicating the path in which the gamma photons direct may be generated, the spatial line may be termed as a LOR 402. The LOR 402 may indicate the gamma photons generated by the annihilation of the radiation source 401.

Figure 5:
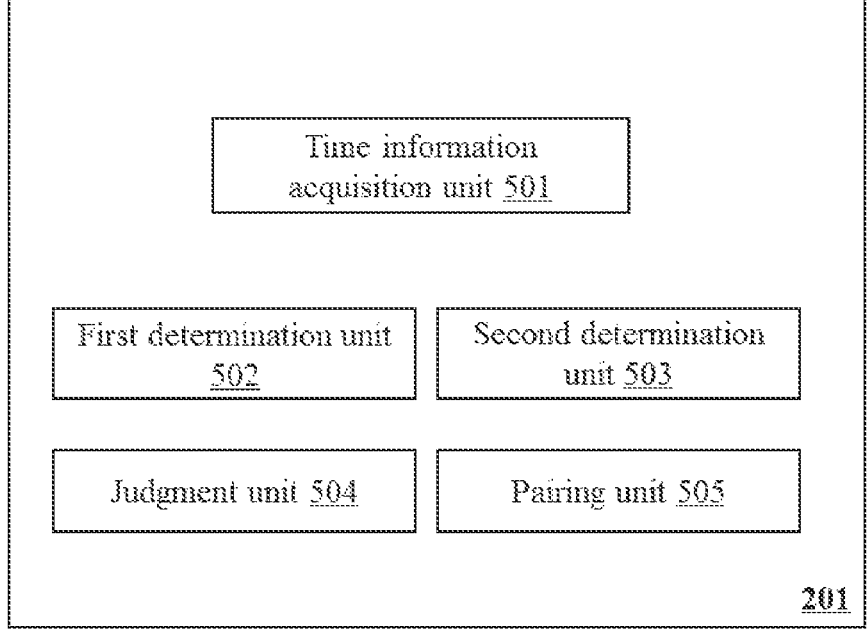
FIG. 5 is a block diagram of a TOF determination module according to some embodiments of the present disclosure.

FIG. 5 is a block diagram of an exemplary TOF determination module 201 according to some embodiments of the present disclosure. The TOF determination module 201 may designate a first photon and a second photon as a photon pair based on the time and location information relating to the first photon and the second photon. The term "photon pair" as used herein may refer to two photons originated from a common annihilation event and generate a coincidence event on the PET scanner. The second photon may be assessed based on a filter window. If the assessment succeeds, the first photon and the second photon may be designated as a photon pair. Otherwise, the second photon may be discarded. After a photon pair is designated, the TOF of the photon pair may be calculated based on the arrival time of photons of the photon pair. In some embodiments, the TOF determination module 201 may include a time information acquisition unit 501, a first determination unit 502, a second determination unit 503, a judgment unit 504, and a pairing unit 505.

The time information acquisition unit 501 may be configured to acquire the time information of the photons. In some embodiments, the time information acquisition unit 501 may acquire the arrival times of a first photon and a second photon that may constitute a coincident photon pair. In some embodiments, a first photon and a second photon of a coincidence event may strike the detector units as described in connection with FIG. 1. The arrival times of the first photon and the second photon may be recorded by the coincidence event detection circuit 150.

The first determination unit 502 and the second determination unit 503 may be configured to determine the location information of the first photon and the second photon. In some embodiments, the first determination unit 502 may be configured to determine the projection point of the first photon in the axial direction of the detector ring 120 and/or the scanning bore 110 as a first projection point. The axial direction of the detector ring 120 and the axial direction of the scanning bore 110 may be essentially the same or essentially parallel to each other. The axis of the detector ring 120 may essentially coincide with or be essentially parallel to the axis of the scanning bore 110. The first determination unit 502 may be configured to determine the projection point of the second photon in the axial direction of the detector ring 120 and/or the scanning bore 110 as a second projection point. As used herein, "essentially," as in "essentially the same," "essentially coincide with," "essentially parallel to," etc., with respect to a parameter or a characteristic may indicate that the variation is within 2%, or 5%, or 8%, or 10%, or 15%, or 20% of the parameter or the characteristic, or an average value of the parameter in, for example, a detector or a PET scanner, etc.

In some embodiments, the second determination unit 503 may be configured to determine the projection point of the first photon in the circumferential direction of the detector ring 120 and/or the scanning bore 110 as a third projection point. The circumferential direction of the detector ring 120 and the circumferential direction of the scanning bore 110 may be essentially the same or essentially parallel to each other. The second determination unit 503 may be configured to determine the projection point of the second photon in the circumferential direction of the detector ring 120 and/or the scanning bore 110 as a fourth projection point.

In some embodiments, the first determination unit 502 and the second determination unit 503 may be combined as a single unit.

The judgment unit 504 may be configured to determine whether the arrival time of the second photon falls within the filter window from the arrival time of the first photon. In some embodiments, the judgment unit 504 may judge whether the distance between the first projection point and the second projection point is less than or equal to a first threshold. The judgment unit 504 may also judge whether the arc length between the third projection point and the symmetry point of the fourth projection point is less than or equal to a second threshold. A symmetry point is described elsewhere in the present disclosure. See, for example, FIGS. 7 and 9 and the description thereof. The first threshold and the second threshold may relate to the size of the filter window. In some embodiments, the first threshold and the second threshold may be selected based on the size of the filter window. For instance, the size of the filter window may be 11*11 width of the crystals; the first threshold and second threshold may be set to be the width of 5 crystals.

In some embodiments, the pairing unit 505 may designate the first photon and the second photon as a photon pair. The TOF of the coincidence event triggered by the first photon and the second photon may be determined based on the information of the photon pair. In some embodiments, if the result of the judgment unit 504 validates the second photon, the first photon and the second photon may be paired. Otherwise, the second photon may be discarded.

Figure 6:
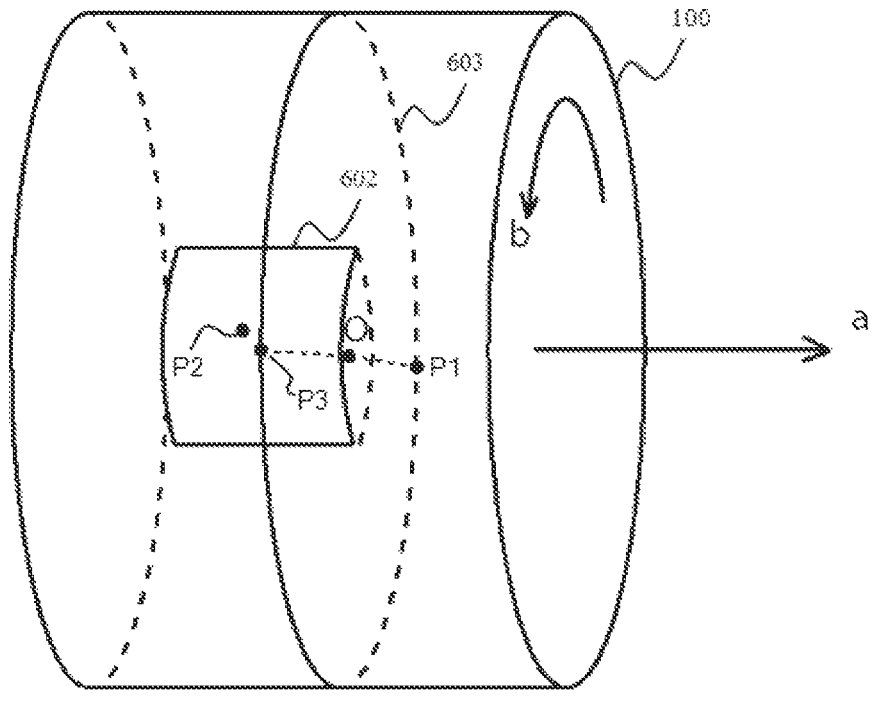
FIG. 6 illustrates a detection of photons in a PET scanner according to some embodiments of the present disclosure.

FIG. 6 illustrates a detection of photons in the PET scanner according to some embodiments of the present disclosure. As shown in the figure, a coincident photon pair (photon P1 and photon P2) generated by annihilation events may be detected by the PET scanner 100. The term "coincident photon pair" as used herein may refer to two photons generated from one or more annihilation event. A filter window 602 may be used to determine whether photon P1 and photon P2 are generated in a same annihilation event based on their positions. In some embodiments, if photon P2 falls into the filter window 602, photon P1 and photon P2 may be designated as a photon pair originated from a same annihilation event. Otherwise, photon P1 and photon P2 may not be designated as a photon pair originated from a same annihilation event, and photon P2 may be discarded.

In some embodiments, the filter window 602 may include a plurality of detector units of the PET scanner 100. In some embodiments, the filter window 602 may include a plurality of crystal elements (or referred as to crystals for brevity) of the PET scanner 100. In some embodiments, the size of the filter window may be determined by the number of detector rings and/or the number of crystal elements of the PET scanner 100. For example, the filter window 602 may include a plurality of crystal elements stretching across one or more detector rings.

In some embodiments, circumference 603 may denote the circumference in which photon P1 is detected in the PET scanner 100, and O may denote the center of the circumference 603. P3 may denote the intersection point between the circumference 603 and the straight line determined by O and photon P1. In some embodiments, the position of the filter window 602 may be determined based on P3. For instance, the center of the filter window 602 may be determined based on P3.

In some embodiments, P3 being designated as the center of the filter window 602 may be symmetric to P1 with respect to the longitudinal center line of the PET scanner 100.

Figure 7:
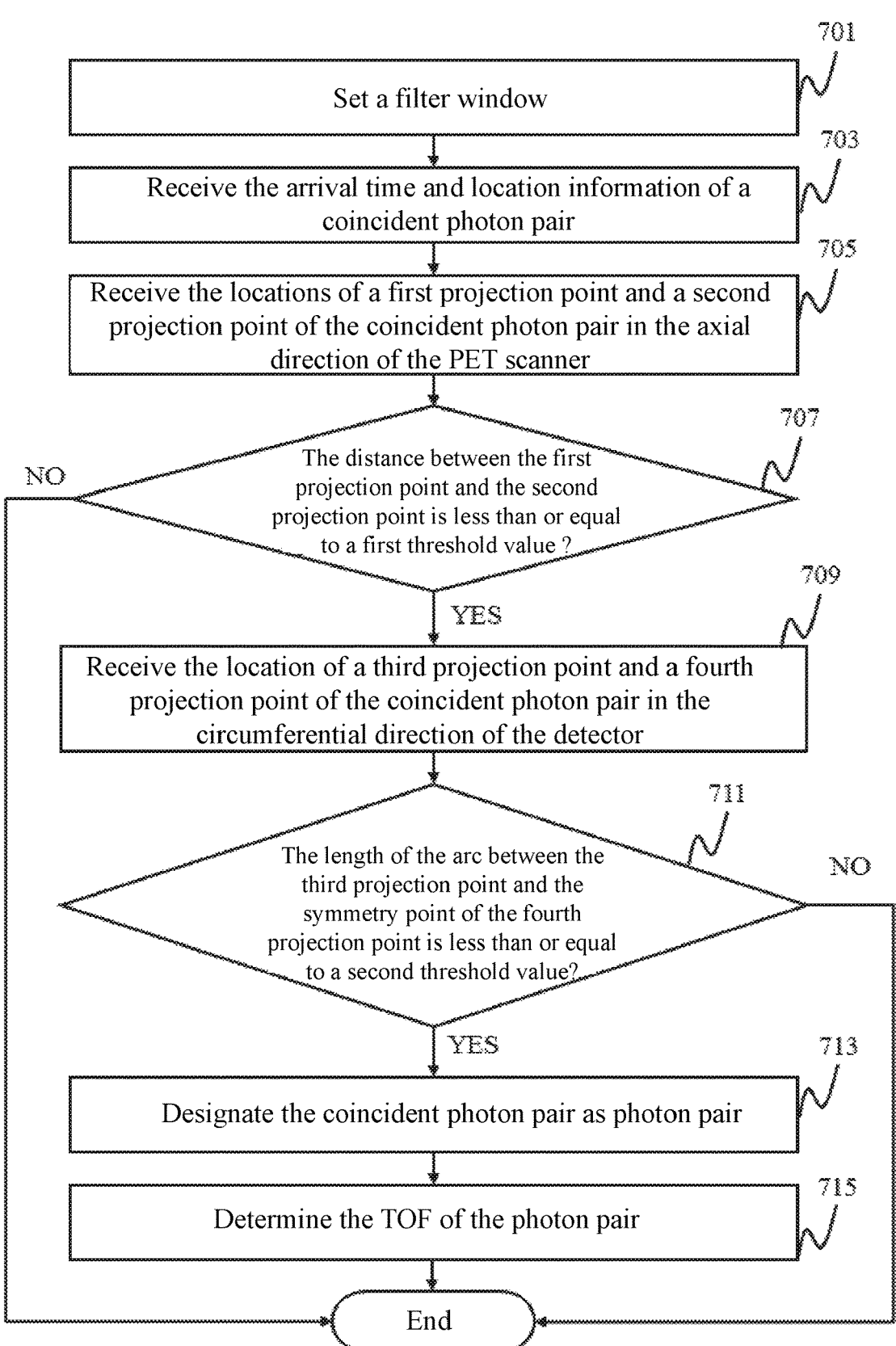
FIG. 7 is a flowchart illustrating a process for TOF determination according to some embodiments of the present disclosure.

FIG. 7 illustrates a flowchart of a process for TOF determination in the PET scanner according to some embodiments of the present disclosure. In step 701, a filter window may be set. In some embodiments, the size of the filter window may be determined by the number of detector rings and the number of crystal elements of the PET scanner. For example, the PET scanner may include 112 detector rings and 112×1152 crystal elements distributed in those 112 detector rings. The filter window may be a portion of the surface of the scanning bore of the PET scanner. The filter window may have a longitudinal width and a circumferential width. For instance, the longitudinal width may be the width of 11 crystal elements, and the circumferential width may be the width of 11 crystal elements as well.

In step 703, the arrival time and location information of a coincident photon pair may be received. In some embodiments, the time and location information of the coincident photon pair may be acquired by the coincidence event detection circuit 150 as described in connection with FIG. 1. In some embodiments, the time and location information may be stored in the storage of the PET scanner, and fetched out for TOF calculation. Two photons may be designated as a photon pair based on their arrival time information. In some embodiments, one photon of the coincident photon pair is designated as a first photon and the other one is designated as the candidate photon to be assessed. In some embodiments, the coincident photon pair may contain P1 and P2.

In step 705, the location information of the projection points of two photons of a candidate coincident photon pair in the axial direction of the PET scanner may be received. In some embodiments, P1 may be the first photon generated in an annihilation event, while P2 may be a candidate photon to be assessed to determine whether P1 and P2 originate from a same annihilation event. In some embodiments, the first projection point may be the projection point of P1 in the axial direction of the PET scanner. The second projection point may be the projection point of P2 in the axial direction of the PET scanner.

Figure 8:
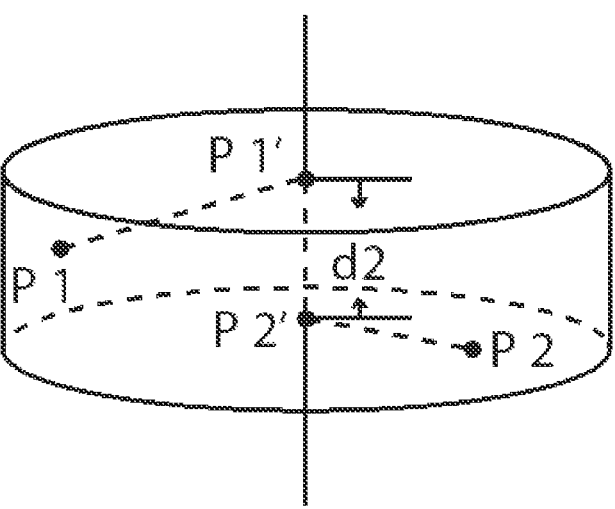
FIG. 8 illustrates a location information of projection points according to some embodiments of the present disclosure.

FIG. 8 illustrates the location information of the first projection point P1' and the second projection point P2'. P1' may denote the first projection point and P2' may denote the second projection point. d2 may denote the distance between P1' and P2'.

Returning to FIG. 7, in step 707, the distance between the first projection point and the second projection point may be assessed based on a first threshold. If the distance between the first projection point and the second projection point (e.g., d2 as illustrated in FIG. 8) is less than or equal to the first threshold, P2 may be further assessed. Otherwise, P2 may be discarded as P1 and P2 are deemed not originated from a same annihilation event.

In some embodiments, the first threshold may correlate with the size of the filter window as described above. In some embodiments, the longitudinal width of the filter window may be the width of m crystal elements, the first threshold may be set as the width of (m−1)/2 crystal elements, wherein m is an odd number. In some embodiment, the first threshold may be the width of 5 crystal elements. In some embodiments, the first threshold may be an even number. It should be noted that the first threshold may be variable and/or adjustable based on the longitudinal width of the filter window. For example, the first threshold may be the width of m crystal elements, the width of (m−1)/a crystal elements, the width of m/a crystal elements, etc., and a may denote an integer.

In step 709, the location information of the projection points of the candidate coincident photon pair in the circumferential direction of the PET scanner may be received. In some embodiments, the third projection point may be the projection point of P1 in the circumferential direction of the PET scanner. The fourth projection point may be the projection point of P2 in the circumferential direction of the PET scanner.

Figure 9:
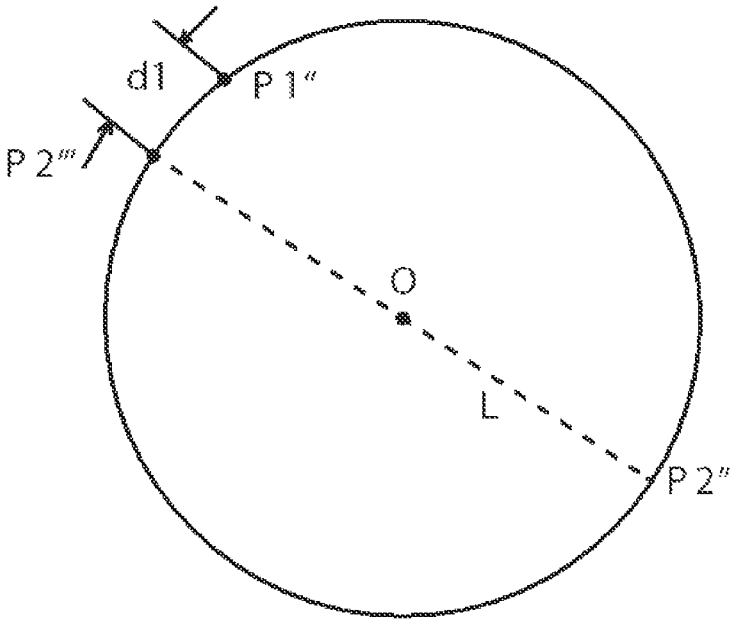
FIG. 9 illustrates a location information of projection points according to some embodiments of the present disclosure.

FIG. 9 illustrates the location information of the third projection point P1″, the fourth projection point P2″, and the symmetry point of the fourth projection point P2‴. d1 may denote the arc length between P1″ and P2‴.

Returning to FIG. 7, in step 711, the distance between P1 and P2 along the circumferential direction may be assess in various ways. In some embodiments, the arc length between the third projection point and the symmetry point of the fourth projection point may be assessed. In some embodiments, the arc length between the third projection point and the symmetry point of the fourth projection point may be calculated. If the arc length between the third projection point and the symmetry point of the fourth projection point is less than or equal to a second threshold, the process may proceed further. Otherwise, P2 may be discarded. In some embodiments, the length of the line segment between the third projection point and the symmetry point of the fourth projection point may be calculated. If the length of the line segment between the third projection point and the symmetry point of the fourth projection point is less than or equal to a second threshold, the process may proceed further. Otherwise, P2 may discarded. In some embodiments, the length of the line segment between the third projection point and the fourth projection point may be calculated. If the difference of the length of the line segment between the third projection point and the fourth projection point, and the diameter of the detector ring is less than or equal to a second threshold, the process may proceed further. Otherwise, P2 may be discarded.

In some embodiments, the second threshold may correlate to the size of the filter window. In some embodiments, the circumferential width of the filter window may be the width of n crystal elements, the second threshold may be set as the width of (n−1)/2 crystal elements, wherein n is an odd number. In some embodiment, the second threshold may be the width of 5 crystal elements. In some embodiments, the second threshold may be an even number. It should be noted that the second threshold may be variable and adjustable based on the circumferential width of the filter window. For example, the second threshold may be the width of n crystal elements, the width of (n−1)/b crystal elements, the width of n/b crystal elements, etc., and b may denote an integer.

After the assessment in step 707 and step 711, the location of the second photon may be determined within the filter window corresponding to the first photon. Thus in step 713, P1 and P2 are designated as a photon pair originated from a common annihilation event. In some embodiments, since the distance between the first projection point and the second projection point is less than or equal to a first threshold, and the arc length between the third projection point and the symmetry point of the fourth projection point is less than or equal to a second threshold, the location of P2 may be determined within the filter window corresponding the location of P1. Thus P1 and P2 may be designated as a photon pair originated from a common annihilation event.

In step 715, the TOF of the photon pair may be determined. The TOF of the photon pair may be determined based on the arrival time information of photons of the photon pair.

In some embodiments, the process for TOF determination above may be used to calculate the average TOF of a crystal element. In some embodiment, all photon pairs of a crystal element may be designated based on the process for TOF determination above. The sum of photon pairs of the crystal element may be calculated. The average TOF may be the ratio of the sum of all TOF and the number of photon pairs. In some embodiments, the average TOF of a crystal element may be calculated based on:

$$\bar{t_j} = \frac{\sum_{i=1}^{sum}(t_{ji} - t_i)}{sum},$$

(Equation 1)

in which j may denote the index number of a crystal elements, i may denote the index number of the photon pair at crystal element j, $\bar{t_j}$ may be the average TOF of crystal element j, $t_{ji}$ may denote the time information (e.g., arrival time) of the first photon of the $i^{th}$ photon pair at crystal element j, $t_i$ may be the time information (e.g., arrival time) of the second photon of the $i^{th}$ photon pair at crystal element j, and sum may denote total number of photon pairs detected by crystal element j. For instance, the PET scanner includes 112 detector rings and 112×1152 crystal elements distributed in those detector rings; each detector ring includes 1152 crystal elements; it may cost 0.561 s to process 9,000,000 coincident photon pairs using a personal computer (PC) with a CPU clock speed of 3.1 GHz and a memory (e.g., ROM) of 4G.

Figure 10:
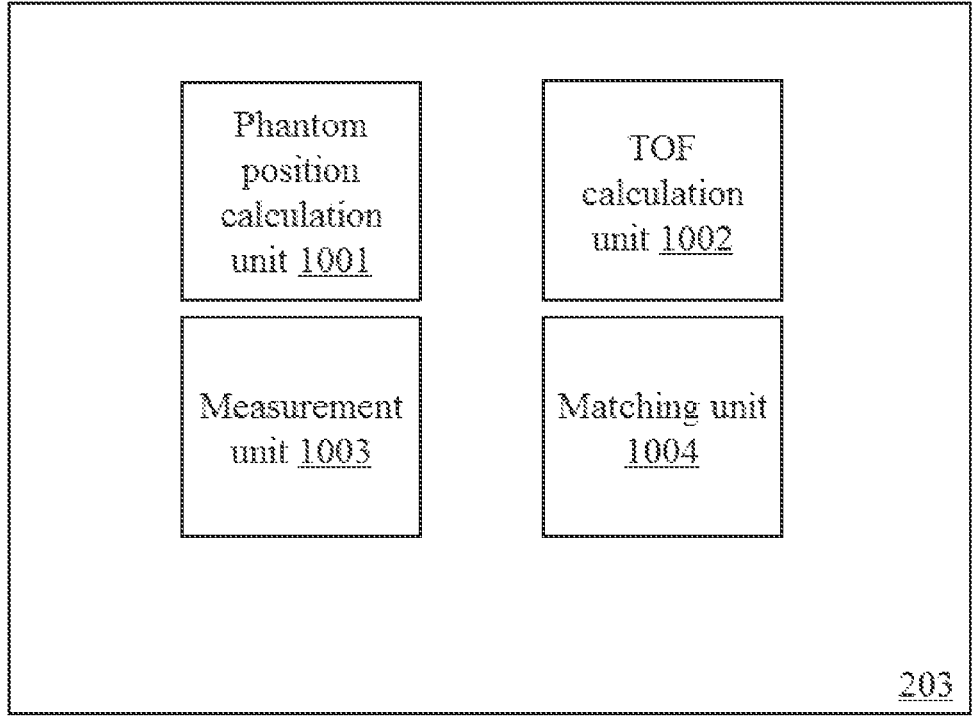
FIG. 10 illustrates a block diagram of a quality determination module according to some embodiments of the present disclosure.

FIG. 10 illustrates a block diagram of the quality determination module 203 according to some embodiments of the present disclosure. The quality determination module 203 may include a phantom position calculation unit 1001, a TOF calculation unit 1002, a measurement unit 1003, and a matching unit 1004.

As shown in FIG. 10, the phantom position calculation unit 1001 may be configured to calculate the location of a phantom. In some embodiments, the phantom may include a radiation source having a shape of a solid rod, a linear radiation source, a radiation source having a shape of a cylinder, or the like, or any combination thereof. The phantom may be located in the field of view (FOV) of the PET scanner and need not be coaxial or concentric with the scanning bore. In some embodiments, an axis (e.g., the longitudinal axis) of the phantom may be parallel to the longitudinal axis of the PET scanner.

The TOF calculation unit 1002 may be configured to calculate a first TOF of an LOR based on the position of the phantom.

The measurement unit 1003 may be configured to calculate a second TOF based on the sinogram of LORs and a time offset table. The time offset table may be prestored in or accessible to the PET scanner. The time offset table may be calibrated based on the sinogram of LORs.

The matching unit 1004 may be configured to assess the first TOF based on the second TOF, and determined the quality of the first TOF. In some embodiments, the assessment may be based on the difference between the first TOF and the second TOF. The difference may be assessed based on a threshold. If the assessment succeeds (e.g., the difference does not exceed the threshold), the first TOF may be validated; otherwise, the first TOF may be invalidated and discarded.

Figure 11:
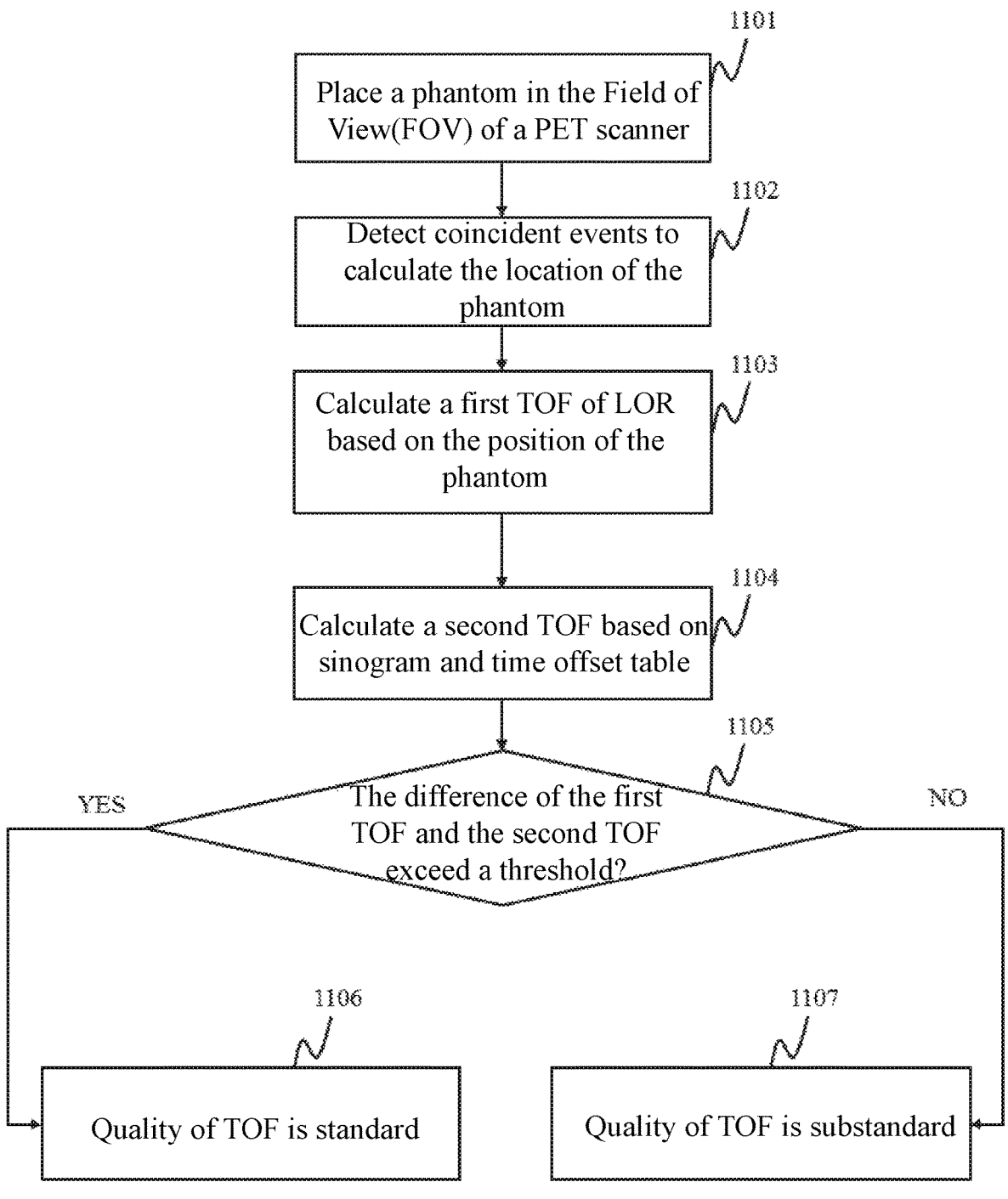
FIG. 11 is a flowchart illustrating a process for TOF quality determination according to some embodiments of the present disclosure.

FIG. 11 is a flowchart illustrating a process for TOF quality determination according to some embodiments of the present disclosure.

In step 1101, a phantom may be placed in the FOV of the PET scanner, the axis of the phantom may be parallel to the longitudinal axis of the PET scanner. In some embodiments, the phantom may be placed in any suitable position in the PET scanner as long as it is located in the FOV of the PET scanner. In some embodiments, the phantom may be concentric with the scanning bore 110 of the PET scanner.

Figure 12:
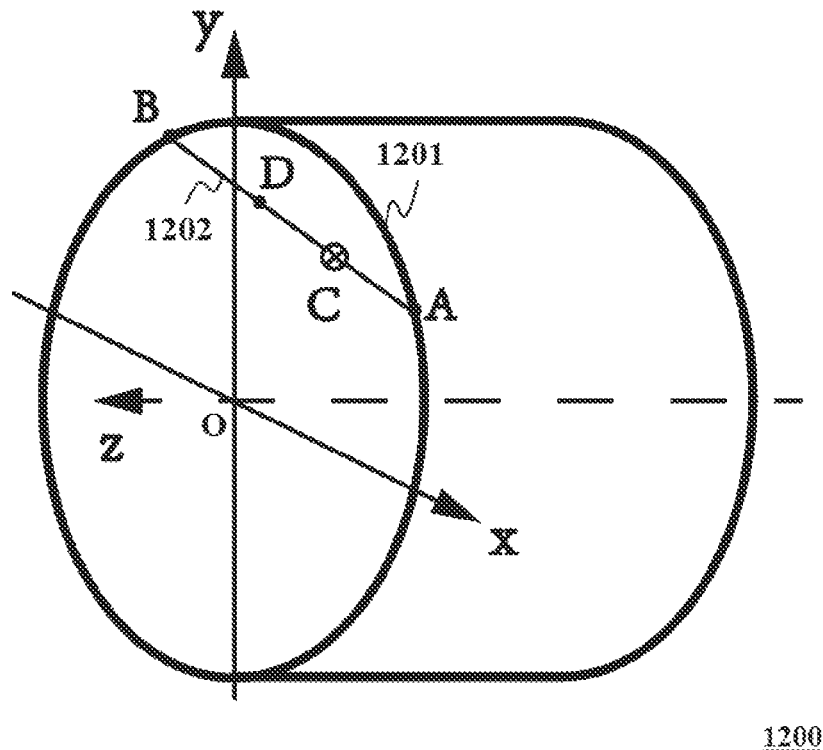
FIG. 12 illustrates an exemplary coordinate system according to some embodiments of the present disclosure.

In step 1102, the position of the phantom may be calculated based on the coincidence events detected by the PET scanner. FIG. 12 illustrates an exemplary coordinate system employed in the scanning bore of the PET scanner according to some embodiments of the present disclosure. The coordinate system may be used to determine the position of the phantom. O may denote the origin of the coordinate system. In some embodiments, O may be the center of the scanning bore. The z-axis may denote the longitudinal axis of the scanning bore 1200. Section 1201 may be a circle indicating the longitudinal section of the scanning bore, and the radius of the section 1201 may be denoted by r. In some embodiments, the section 1201 may be a detector ring. The scanning bore 1200 may include a plurality of detector rings configured to detect gamma photons generated by annihilation events. In some embodiments, a detector ring may include a plurality of detector units including crystal elements and/or crystal element array(s) the term "crystal element array" as used herein may refer to an array of crystal elements.

In some embodiments, a detector ring may include a plurality of crystal elements. For example, two photons of a coincidence event may be detected by a crystal element A($X_a$, $Y_a$) and a crystal element B($X_b$, $y_b$), respectively. The line segment connecting crystal element A($X_a$, $Y_a$) and crystal element B($X_b$, $Y_b$) may be the LOR of the coincidence event. In some embodiments, the LOR processor as described in connection with FIG. 1 may be used to determine the LOR. In some embodiments, the phantom position calculation unit 1001 as described in connection with FIG. 10 may be configured to calculate the position of the phantom on the LOR based on the arrival time of the two photons striking the two crystal elements. The position of the phantom may be denoted as ($X_0$, $Y_0$), wherein $0 < X_0 < r$ and $0 < Y_0 < r$. In some embodiments, the TOF processor as described in connection with FIG. 1 may calculate the TOF of the coincidence event. The TOF may be used to determine the position of the phantom.

In step 1103, a first TOF of the LOR may be calculated based on the position of the phantom calculated in step 1102. Referring to FIG. 12, two photons originated from a same annihilation event occurred in the phantom C may strike crystal element A and crystal element B to generate a coincidence event. LOR 1202 (line segment AB) may denote the LOR of the coincidence event, and D may denote the center of AB. The x-y plane may denote the longitudinal section of the scanning bore 1200. The z-axis may denote the longitudinal axis of the scanning bore 1200. The z-axis may be perpendicular to the x-y plane. The distance between C and D may be calculated by:

$$\Delta l = y_0 \cos \varphi - x_0 \sin \varphi, \ (-\pi \le \varphi \le +\pi), \quad \text{(Equation 2)}$$

in which φ may denote the included angle of the LOR 1202 and y-axis, and Δl may denote the distance between C and D. Therefore, the difference of line segment BC (the distance of the phantom C and the crystal element B) and line segment AC (the distance of the phantom C and the crystal element A) may be calculated by:

$$\Delta s = 2\Delta l = 2(\Delta l = y_0 \cos \varphi - x_0 \sin \varphi), \quad \text{(Equation 3)}$$

in which Δs may denote the difference of line segment BC and line segment AC. Therefore, the TOF of the LOR 1202 may be calculated by:

$$\Delta t = \frac{2(y_0 \cos \varphi - x_0 \sin \varphi)}{c}, \quad \text{(Equation 4)}$$

in which Δt may denote the first TOF of the LOR 1202, and c may denote the light speed.

In some embodiments, Equation 2, Equation 3, and Equation 4 may be used to calculate first TOF of a plurality of LORs generated by the phantom, and a curve of Δt may be generated based on the first TOF of the LORs. In some embodiments, Equation 2, Equation 3, and Equation 4 may be used to calculate first TOFs of at least some LORs generated by the phantom, and a curve of Δt may be generated based on the first TOFs of these LORs.

In step 1104, a second TOF of an LOR may be calculated based on a sinogram and a time offset table.

In some embodiments, a time offset table may be prestored in the storage of the PET scanner or otherwise accessible by the PET scanner. The time offset table may be used to improve the resolution of the PET scanner for the calculation of a TOF. Referring to FIG. 12, the measurement TOF of an coincidence event may be calculated by:

$$\Delta \tau_{AB} = (T_A - OT_A) - (T_B - OT_B) = (T_A - T_B) - (OT_A - OT_B), \quad \text{(Equation 5)}$$

in which $OT_A$ may denote the time offset of crystal element A, and $OT_B$ may denote the time offset of crystal element B. ($OT_A - OT_B$) may be calculated by looking up the time offset table. $T_A$ may denote the arrival time at crystal element A, while $T_B$ may denote the arrival time at crystal element B. The time offset table may be indexed according to the index number of the crystal element. For example, crystal element A may have a time offset in the time offset table, and the index number of the time offset may be denoted by A.

In some embodiments, the PET scanner may acquire a plurality of LORs in different angles, and create a sinogram of these LORs. In some embodiments, the time offset table may be calibrated based on the sinogram.

In some embodiments, a histogram of a plurality of LORs of the PET scanner may be created. The second TOF may be calculated based on the histogram. The second TOF of an LOR may be calculated by:

$$\Delta t' = \frac{\sum_i \Delta \tau_i n_i}{\sum_i n_i},$$

(Equation 6)

in which the bin of the histogram may cover the range from 5 picoseconds to 15 picoseconds. $\Delta t'$ may denote the second TOF. In some embodiments, the bin may be 10 picoseconds. In Equation 6, i may denote the index number of histogram, $n_i$ may denote the number of coincidence events in the $i^{th}$ histogram, and $\Delta \tau_i$ may denote the measured TOF of coincidence events in the $i^{th}$ histogram.

Figure 13:
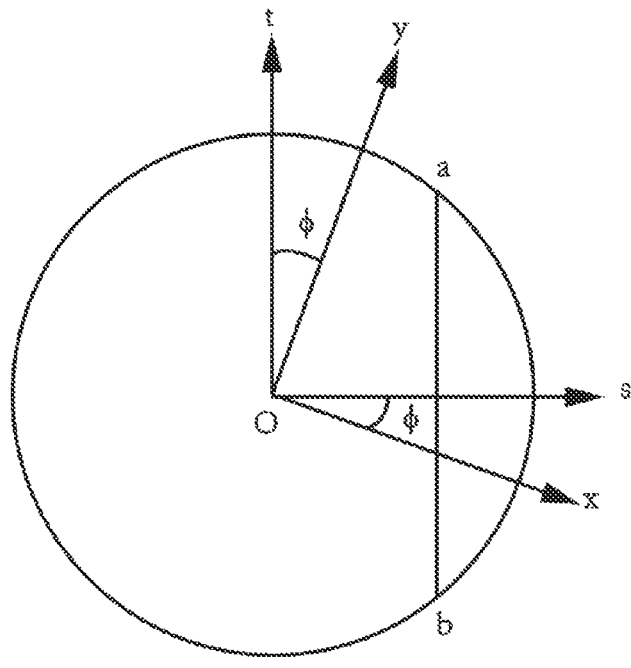
FIG. 13 illustrates an exemplary coordinate system according to some embodiments of the present disclosure.

FIG. 13 illustrates an exemplary coordinate system that may be employed in the scanning bore according to some embodiments of the present disclosure. As shown in the figure, a TOS coordinate system corresponding to an LOR ab may be created on a xOy plane. The t-axis may be parallel to ab, and the s-axis may be perpendicular to ab and intersect with ab at the center point of ab. $(r_a, r_b, \varphi_j, s_j)$ may denote an LOR in the sinogram, in which j may denote the index number of the LOR, (j=1, 2, 3 . . . 576), $\varphi_j$ may denote the included angle between the LOR and the y-axis, and $s_j$ may denote the distance between the LOR and the center of the scanner bore (O as shown in the figure). ra and rb may denote the two crystal elements corresponding to the LOR, respectively. In some embodiments, a plurality of LORs may correspond to a pair of crystal elements. In some embodiments, a curve of $\Delta t'$ may be generated according to Equation 6.

In step 1105, the curve of $\Delta t$ generated according to Equation 4 may be assessed based on the curve of $\Delta t'$ to determine the quality of the first TOF. The curve of $\Delta t$ may include a plurality of first TOFs of LORs, while the curve of $\Delta t'$ may include a plurality of second TOFs of LORs. A threshold may be set to assess a first TOF based on the corresponding second TOF for a same LOR. If the difference between the first TOF and the corresponding second TOF exceeds the threshold, the first TOF may be validated, otherwise, the first TOF may be invalidated and discarded.

Figure 14A:
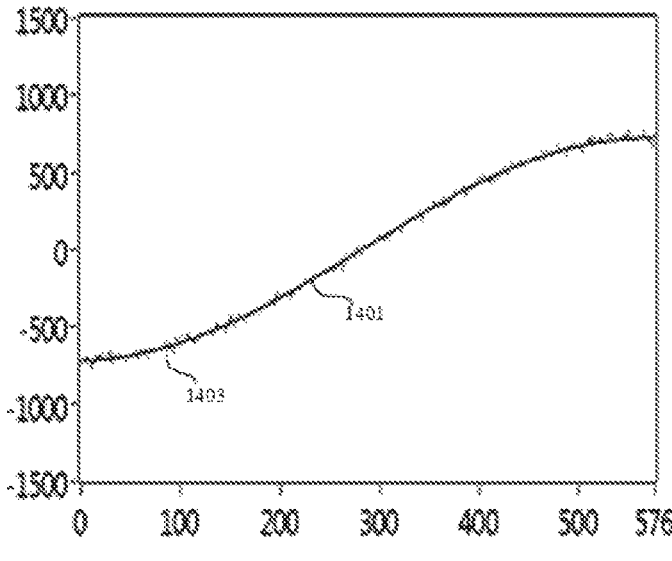
FIG. 14A and FIG. 14B illustrate two diagrams of TOF quality according to some embodiments of the present disclosure.

FIG. 14A illustrates a diagram of validated first TOFs according to some embodiments of the present disclosure. The horizontal axis denotes the index number of LOR. The vertical axis may denote a TOF of an LOR. The smooth curve 1401 may indicate first TOFs, while the coarse curve 1403 may indicate second TOFs. Merely by way of example, the threshold may be set to be 25 picoseconds. The smooth curve 1401 and the coarse curve 1403 may be assessed by:

$$|\Delta t - \Delta t'| \le 25 \text{ picoseconds.}$$

(Equation 7)

If the absolute value of the difference between a first TOF and the corresponding second TOF is less than or equal to 25 picoseconds, the first TOF is validated.

Figure 14B:
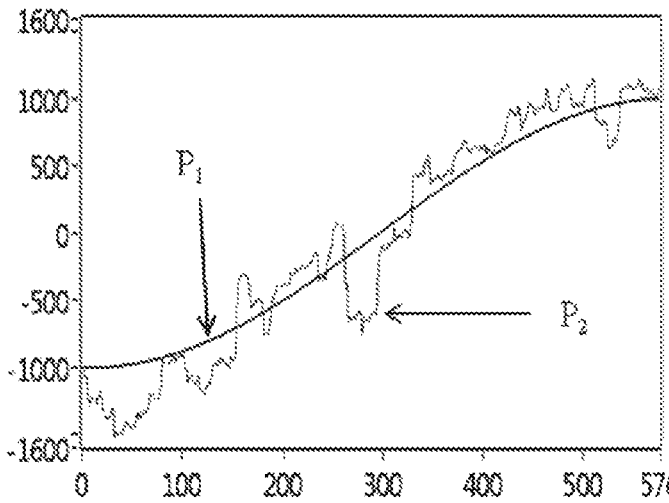

FIG. 14B illustrates a diagram of invalidated first TOFs according to some embodiments of the present disclosure. As shown in the figure, curve P1 denotes first TOFs, while curve P2 denotes second TOFs. It may be seen from the figure that the deviation of curve P2 from curve P1 is larger than that illustrated in FIG. 14A. In some embodiments, the first TOFs in FIG. 14B may be invalidated.

In some embodiments, the phantom may be placed in the center of the scanning bore, e.g., being concentric with the scanning bore. In some embodiments, the phantom may not be concentric with the scanning bore. In some embodiments, the PET scanner may further include a calibration module configured to calibrate first TOFs when the first TOF is invalidated based on corresponding second TOFs. For example, if a first TOF is invalidated, the value of the first TOF may be reassigned based on the value of the corresponding second TOF.

Figure 15:
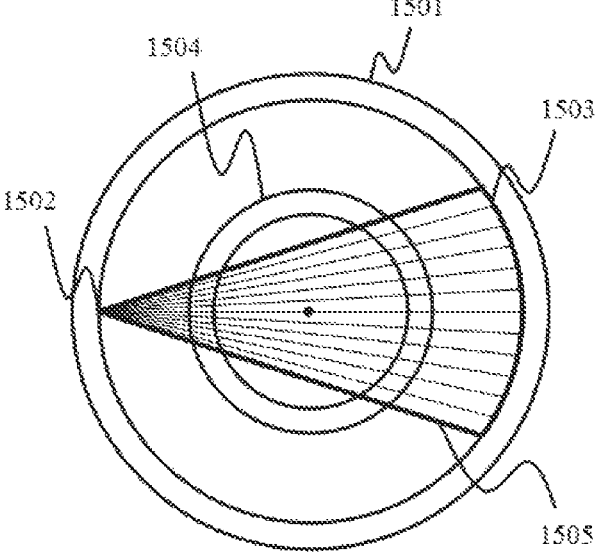
FIG. 15 illustrates an exemplary phantom according to some embodiments of the present disclosure.

FIG. 15 illustrates an exemplary phantom according to some embodiments of the present disclosure. The time calibration of a plurality of detector units in a PET scanner may be performed using the phantom. In some embodiments, a first crystal element 1502 and multiple second crystal elements 1503 may be set inside a cylindrical bore 1501. In some embodiments, the first crystal element 1502 and multiple second crystal elements 1503 may form multiple crystal element pairs. A crystal element pair may include the first crystal element 1502 and a second crystal element 1503 of the multiple second crystal elements. The first crystal element 1502 and the second crystal element 1503 may receive a photon of a coincidence event, respectively. A phantom 1504 filled with a radiation source may be placed inside the bore 1501. Annihilation events may occur in the phantom 1504. In some embodiments, the center of symmetry of the phantom may be placed at the center of the FOV of the PET scanner and the center axis of the phantom 1504 and that of the bore 1501 may coincide. In some embodiments, all of the plurality of detector units in the PET scanner, including the first crystal element 1502 and the multiple second crystal elements 1503, may define a center axis that coincides with the center axis of the bore 1501. In some embodiments, the center of symmetry of the phantom may not be placed at the center of the FOV of the PET scanner. For example, the center axis of the phantom 1504 may be parallel to but at a distance from the center axis of the bore 1501. The ratio of the distance between the center axis of the phantom 1504 and the center axis of the bore 1501 to $D_{FOV}$ may be within a specific ratio range, where $D_{FOV}$ may denote the length of the FOV in the radial direction. The ratio range may range from 0.1 to 0.8, from 0.2 to 0.7, or from 0.3 to 0.5. As another example, the center axis of the phantom 1504 may not be parallel to the center axis of the bore 1501. An inclined angle formed between the center axis of the phantom 1504 and the center axis of the bore 1501 may range from 0° to 90°, from 10° to 70°, from 20° to 50°, or from 30° to 40°. In some embodiments, the shape of the phantom 1504 may be symmetric. For example, the phantom 1504 may have the shape of a hollow cylinder. In such cases, the phantom 1504 may be referred to as a hollow cylindrical phantom, whose cross section along the axial direction may be a hollow circular ring. The radiation source may be filled within or at least partially filled within the space defined between the outer surface and the inner surface of the hollow cylinder. As another example, the cross section of the phantom 1504 along the axial direction may have the shape of a hollow elliptic ring, which has a long axis and a short axis. As still another example, the cross section of the phantom 1504 along the axial direction may have the shape of a hollow square, a hollow rectangle, or the shape with at least one axis of symmetry. In some alternative embodiments, the shape of the phantom may be asymmetric. For example, the cross section of the phantom 1504 along the axial direction of the bore 1501 may be asymmetric, without any axis of symmetry. In some embodiment, the thickness of the portion of the phantom 1504 filled with the radiation source may be uniform. In some embodiment, the thickness the portion of the phantom 1504 filled with the radiation source may be non-uniform. The size of the phantom 1504 may correlate to the size of the FOV of the PET scanner. In some embodiments, the diameter of the phantom 1504 may range from $D_{FOV}/2$ to $D_{FOV}$, where $D_{FOV}$ may denote the length of the FOV in the radial direction. In some embodiments, the phantom length in the axial direction may be equal to or not equal to the length of the FOV in the axial direction. For example, the phantom length in the axial direction may be less than or larger than the length of the FOV in the axial direction.

FIG. 16 is a flowchart illustrating a process for time calibration for the PET scanner according to some embodiments of the present disclosure. In the process the TOF of the two photons in a coincidence event is calculated. The process may be repeatedly performed to calibrate every crystal element in the PET scanner. Thus the time offset for multiple crystal elements may be determined. In step 1601, a hollow cylindrical phantom may be placed at the center of the FOV of the PET scanner. In some embodiments, the time offset of the PET scanner may be cleared. In some embodiments, all the electrical time offset of the PET scanner may be cleared.

In step 1603, a first crystal element may be selected from a detector ring of the PET scanner. The first crystal element may be selected for the calibration of its time offset, and n second crystal elements may be selected from the detector ring of the PET scanner to form n crystal element pairs with the first detector unit. In some embodiments, n may denote an integer. In some embodiments, n LORs may be determined based on the first crystal element and the n second crystal elements.

In some embodiments, A may denote a first crystal element, and $B_i$ may denote a second crystal element that may detect a coincidence event with A. i may denote the index number of the second crystal element, and i may range from 1 to n. In some embodiments, $LOR_1$ may denote the LOR between the first crystal element A and the second crystal element $B_1$. $LOR_2$ may denote the LOR between the first crystal element A and the second crystal element $B_2$. Likewise, $LOR_n$ may denote the LOR between the first crystal element A and the second crystal element $B_n$. In some embodiments, the LORs of the first crystal element and n second crystal elements $B_1$ through $B_n$ may form a sector area 1505 as shown in FIG. 15. In some embodiments, the LORs may pass through the hollow cylindrical phantom 1504 filled with a radiation source. The relative location of the first crystal element and the corresponding second crystal element may be determined based on the dimension of the reconstructed PET image. For a two-dimensional image reconstruction, the first crystal element and the multiple second crystal elements may be located in a same detector ring. For a three-dimensional image reconstruction, the first crystal element and the multiple second crystal elements may be located in a same detector ring or different detector rings. For example, the first crystal element and the multiple second crystal elements may be located in different detector rings.

Figure 17:
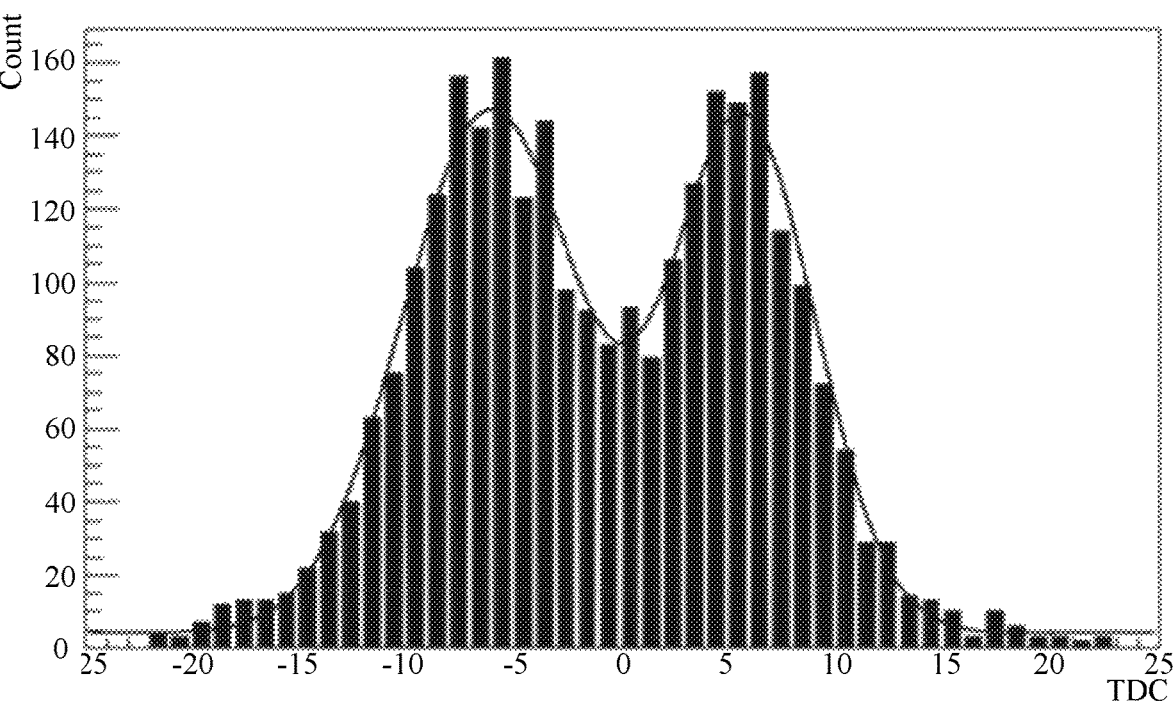
FIG. 17 illustrates a histogram relating to LOR according to some embodiments of the present disclosure.

In step 1605, the TOF of a coincident photon pair detected between the first crystal element and a corresponding second crystal element may be calculated. In some embodiments, m coincidence events may be detected by the first crystal element and the corresponding second crystal element. Therefore, m TOFs may be acquired. A histogram of the m TOFs may be created (FIG. 17). The n crystal element pairs may receive coincident photon pairs and their time information.

FIG. 17 illustrates a histogram relating to the first crystal element and the corresponding second crystal element according to some embodiments of the present disclosure. The horizontal axis of the histogram may denote time distribution of the accumulation of coincidence events, and the bin width may be set to 5 picoseconds. In some embodiments, the bin width may be defined by a user. The vertical axis of the histogram may denote the number of coincidence events (also referred to as the coincidence event counts) within a certain period of time. The histogram may represent the relationship between TOFs and corresponding coincidence event counts relating to the TOFs. The histogram as illustrated in FIG. 17 may be symmetric and have two peaks.

In some embodiments, the histogram may be axisymmetric. For example, by placing an asymmetric phantom in the FOV, it may produce a histogram with axisymmetric shape. In some embodiments, the center of the symmetry of the histogram may be T=0. For example, by placing a symmetric phantom (e.g., a hollow cylindrical phantom) at the center axis of the bore 1501, it may produce a histogram whose center of the symmetry is at the position of T=0. In some embodiments, the center of the symmetry of the histogram may not be T=0. For example, by placing a symmetric phantom (e.g., a hollow cylindrical phantom) at a distance from the center axis of the bore 1501, it may produce a histogram whose center of the symmetry is away from the position of T=0. In some embodiments, the crest factor of the two peaks may be different.

In step 1607, a time value $T_c$ may be calculated. In some embodiments, Tc may be the time value of the center of the symmetry of the histogram. In some embodiments, $T_c$ may be calculated by:

$$T_c = \frac{1}{m}\sum TOF_{Aj} - TOF_{Bj}, \qquad \text{(Equation 8)}$$

in which $TOF_{Aj}$ may denote the arrival time of a photon of a coincidence event in respect to crystal element A, $TOF_{Bj}$ may denote the arrival time of another photon of a candidate coincidence event in respect to crystal element B, m may denote the number of coincidence events detected by crystal element A and crystal element B, and j may denote the index number of a coincidence event detected by crystal element A and crystal element B where j=1, 2, 3, . . . , m.

In some embodiments, $T_c$ may also be determined based on the time value at the two peaks in the histogram. For example $T_c$ may be calculated by:

$$T_c = (T_1 + T_2)/2, \qquad \text{(Equation 9)}$$

in which $T_1$ and $T_2$ may denote the time value at the two peaks in the histogram as illustrated in FIG. 17. In some embodiments, step 1607 may be repeatedly performed to calculate n time values $T_c$ for the n crystal element pairs including the first crystal element and the n second crystals.

In step 1609, the time offset of the first crystal element may be calculated based on the time values $T_c$ obtained in step 1607. In some embodiments, the time offset of the first crystal element may be calculated by:

$$OTA_i = OTA_{i-1} + Tc_i. \qquad \text{(Equation 10)}$$

i may denote the index number of the iteration, and i=1, 2, 3, 4, . . . , n. OTA may denote the time offset of the first crystal element. In some embodiments, $OTA_1$=0. The iteration may terminate based on a criterion. In some embodiments, the criterion may be the number of iterations.

In some embodiments, the process from step 1601 to step 1609 may be repeatedly performed to calculate the time offset of a plurality of crystal elements in a detector ring of the PET scanner. In some embodiments, the process from step 1601 to step 1609 may be repeatedly performed to calculate the time offset of a plurality of detector rings of the PET scanner.

In some embodiments, the first crystal element and n second crystal elements may be located in two detector rings of the PET scanner.

In some embodiments, TOFs acquired by the crystal elements may be calibrated based on the time offset $OTA_k$, where k may denote the index number of a crystal element. TOF may be calibrated by:

$$TOF'_k = TOF_k - OTA_k. \qquad \text{(Equation 11)}$$

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the histogram described above is merely provided for illustrating the relationship between the TOFs and coincidence event counts relating to the TOFs. For persons having ordinary skills in the art, the relationship between the TOFs and coincidence event counts relating to the TOFs can be represented by other forms of diagrams or graphs, e.g., a fitted curve, a list.

Figure 18:
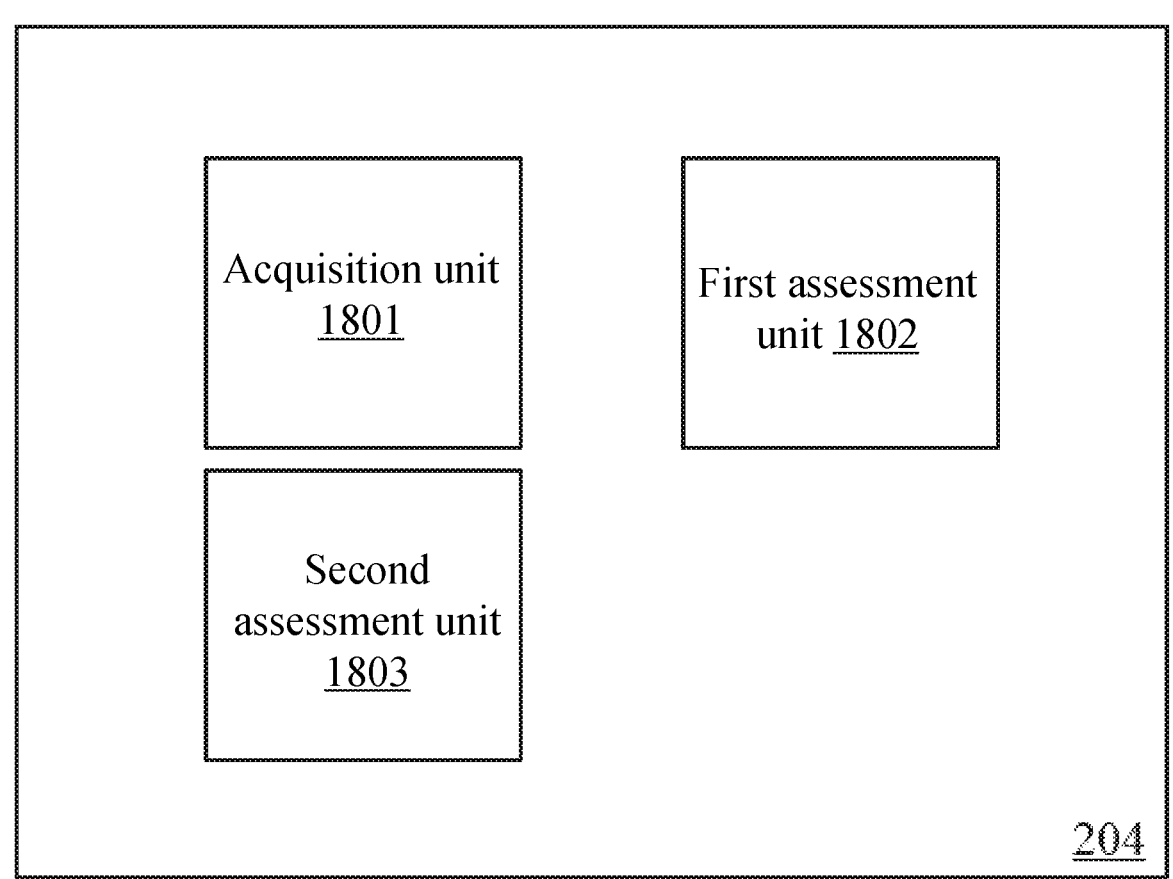
FIG. 18 is a block diagram of a radiation source adjustment module according to some embodiments of the present disclosure.

FIG. 18 illustrates a block diagram of the radiation source adjustment module 204 according to some embodiments of the present disclosure. The radiation source adjustment module may include an acquisition unit 1801, a first assessment unit 1802, and a second assessment unit 1803.

The acquisition unit 1801 may be configured to acquire the position of a radiation source placed in the PET scanner. The first assessment unit 1802 may be used to assess the axial position of the radiation source. The second assessment unit 1803 may be used to assess the circumferential position of the radiation source.

In some embodiments, the position of the radiation source may be assessed based on a target position. The target position may include a target axial position and a target circumferential position.

Figure 19:
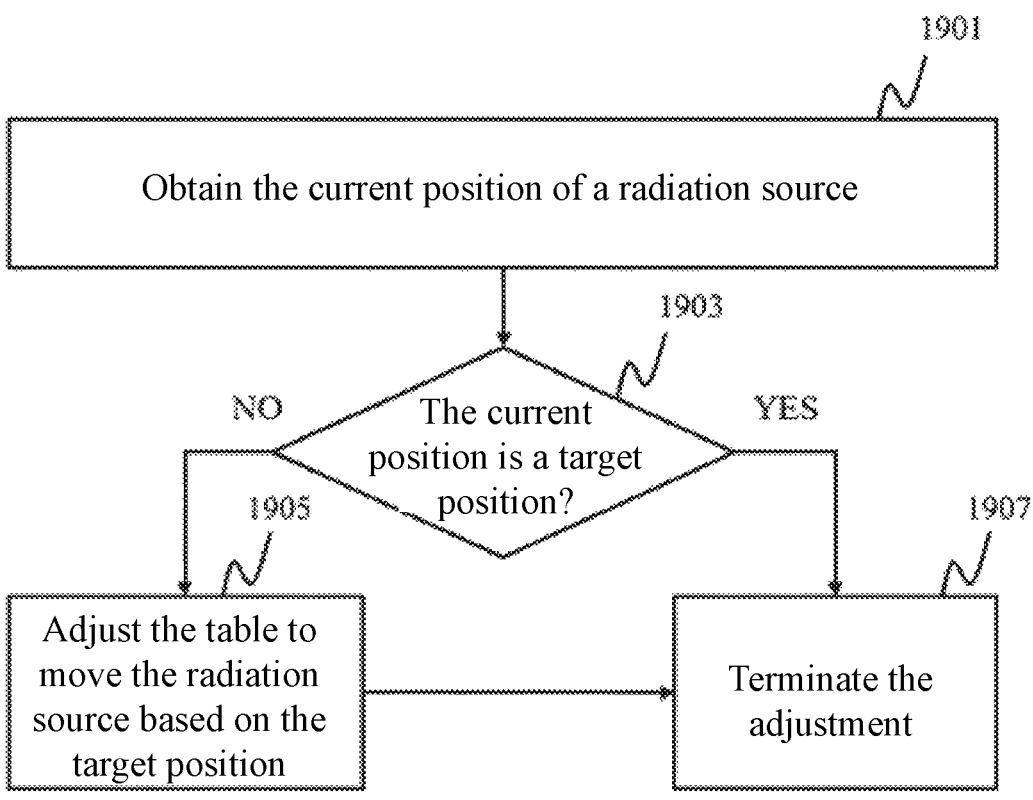
FIG. 19 is a flowchart illustrating a process for radiation source adjustment according to some embodiments of the present disclosure.

FIG. 19 is a flowchart illustrating a process for radiation source adjustment according to some embodiments of the present disclosure. The radiation source may include a solid rod radiation source, a cylinder radiation phantom, a uniform water radiation source (water mixed with a radiation source) placed in a cylindrical tube, or the like, or any combination thereof. The process for radiation source adjustment may be used to adjust the position of a radiation source placed in the PET scanner.

In step 1901, the current position of a radiation source may be obtained. The radiation source may be placed on the table 140 as described in connection with FIG. 1. The current position of the radiation source may be sent to the host computer 160 as described in connection with FIG. 1. In step 1903, the current position of the radiation source may be assessed based on a target position. In some embodiments, the target position may be the central point in the FOV of the PET scanner. In step 1905, if the current position of radiation source is not the target position, the host computer 160 may control the movement of the table 140 based on the target position. In step 1907, the adjustment of the radiation source may be terminated if the current position of the radiation source is the target source.

Figure 20:
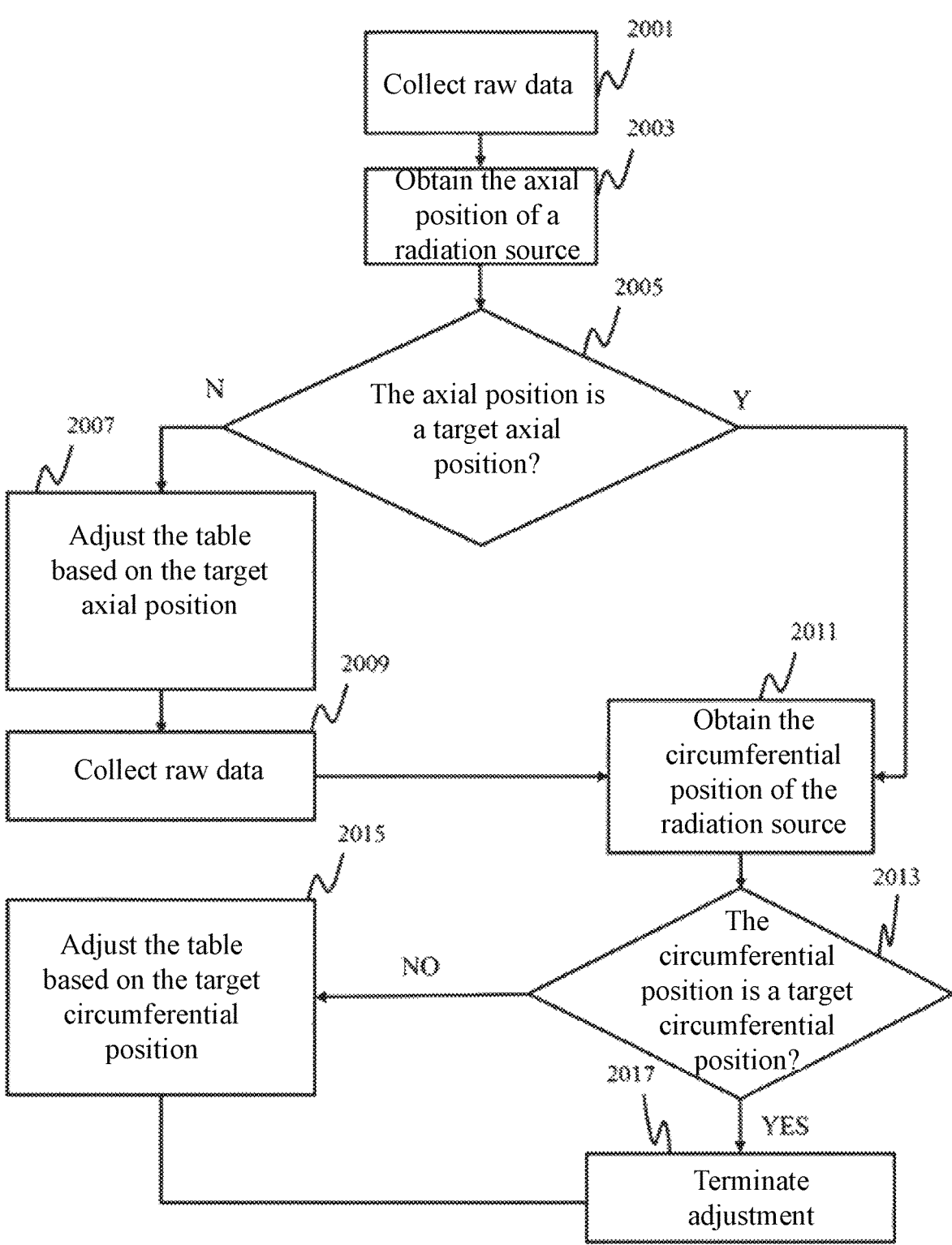
FIG. 20 is a flowchart illustrating a process for radiation source adjustment according to some embodiments of the present disclosure.

FIG. 20 is a flowchart illustrating a process for radiation source adjustment according to some embodiments of the present disclosure. In step 2001, raw data may be collected by the PET scanner. For instance, raw data ranging from 10 megabytes to 15 megabytes may be collected. In step 2003, the axial position of a radiation source may be obtained. In step 2005, the axial position of the radiation source may be assessed based the target axial positon. In step 2007, the table may be adjusted to move the radiation source based on the axial target position.

In some embodiments, the scanning bore 110 as described in connection with FIG. 1 may be divided into a number of portions based on the number of detector rings of the PET scanner. The division may be even such that the portions are of a same size. The difference for a portion may be calculated. In some embodiments, the difference for the portion may be the difference between the prompt coincidence counts and the delay coincidence counts of the raw data. The prompt coincidence counts may include true coincidence events, random coincidence events, and scatter coincidence events. The delay coincidence counts may include random coincidence events. Therefore, the difference of the portion may be the count of true coincidence events and scatter coincidence events. A first threshold may be set. The scanning bore of the PET scanner may be divided into equal parts. The first difference value that may be greater than the first threshold may be acquired as one endpoint of the radiation source when searching from the forward equal part to the middle of the scanning bore and the first difference value that may be greater than the first threshold may be acquired as other endpoint of radiation source when searching from the backward equal part of the scanning bore to the middle of the PET detector, the position of the radiation source may be acquired according to the above steps as described.

Merely by way of example, the PET scanner may include 96 detector rings. The scanning bore 110 may be divided into 96 portions evenly. The differences of the portions may be calculated and a waveform of the differences may be created. The waveform indicates that the difference of the portion in which the radiation is located may be much larger than the difference of the rest portions in which the radiation source is not located. In some embodiments, d may denote the largest difference of the portions. The first threshold t may be calculated by:

$$t = d * 0.25. \qquad \text{(Equation 12)}$$

An assessment of the 96 portions from the $1^{st}$ portion to the $96^{th}$ portion may be performed. Two portions of the 96 portions may be selected for determining both ends of the radiation source if the first threshold is satisfied. If the two portions are the $1^{st}$ portion and the $96^{th}$ portion, the axial position of the radiation source may be validated indicating the target axial position is satisfied. Otherwise, the axial target position is not satisfied and the host compute may instruct the table to move the radiation source based on the axial target position. In some embodiments, the portions may be divided based on the length of the scanning bore. As the length of the scanning bore is knows, the length of a portion may be known as well. The radiation source may be moved based on the length of one or more portions, for example, the length of 1 portion, the length of 32 portions, or the like.

If the assessment of step 2005 is validated, step 2011 may be performed and the circumferential position of the radiation source may be obtained. Otherwise, raw data may be collected in step 2009. In step 2009, raw data may be collected by the PET scanner. In some embodiments, raw data ranging from 10 megabytes to 15 megabytes may be collected.

In step 2011, the circumferential position of the radiation source may be obtained.

In some embodiments, 2m−1 sinograms may be obtained, in which m may denote the number of detector rings of the PET scanner. For instance, the PET scanner may include 96 detector rings, and therefore, 191 sinograms may be obtained.

In some embodiments, the 2m−1 sinograms may be divided into a number of groups evenly. For a group of the number of groups, the sinograms of the group may be accumulated to generate an accumulated sinogram. In some embodiments, each sinogram of the group may be denoted by a two-dimensional (2D) array; an accumulated sinogram may be generated by adding the numbers corresponding to a same row position and a same column position of the 2D arrays together. The center of the radiation source at every angle of the accumulated sinogram may be obtained based on the Gaussian function and the accumulated sinogram. The center of the radiation source in every angle of the accumulated sinogram may be fitted based on a sine wave and be corrected based on geometry radian, to generate the circumferential position of the radiation source.

In some embodiments, the circumferential position of all the groups may be fitted based on a straight line to acquire the center line of the radiation source. The center line of the radiation source may be assessed based on the center line of the FOV of the PET scanner.

Figure 21:
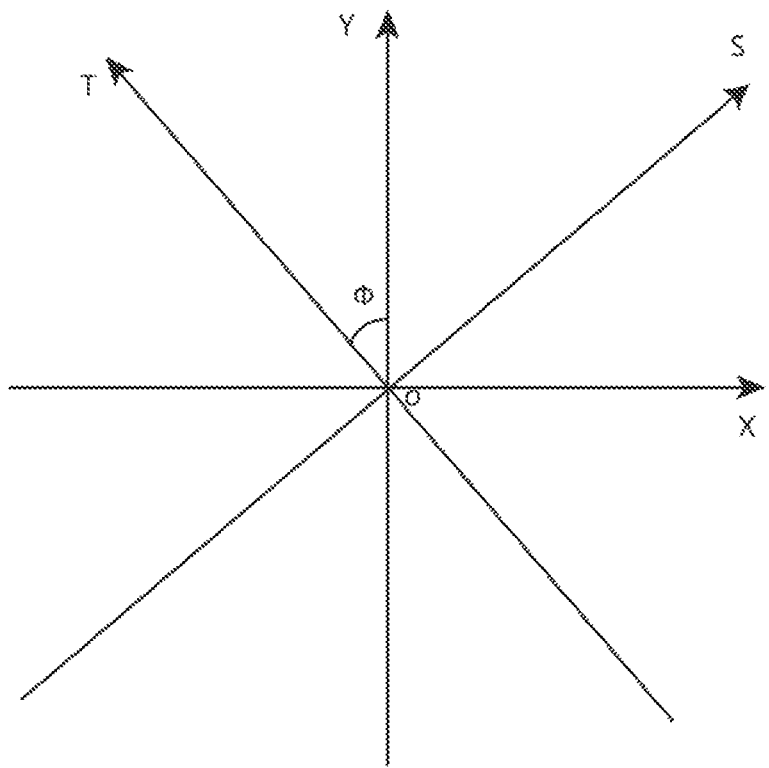
FIG. 21 illustrates an exemplary coordinate system for a sinogram according to some embodiments of the present disclosure.

In some embodiments, as illustrated in FIG. 21, a sinogram may be a two-dimensional array whose row and column may be denoted by S and $\Phi$, respectively. S may denote the distance from the center of the FOV (corresponding to the coordinate origin O in FIG. 21) to the LOR, and $\Phi$ may denote the angle between LOR and the y-axis.

In some embodiments, n sinograms may be divided into t groups, and each group may have d (t=n/d) sinograms. d sinograms may be accumulated in each group, and t accumulated sinograms may be generated. For an accumulated sinogram, the center of the radiation source at an angle may be calculated based on Gaussian fitting. Therefore, t centers of the radiation source may be obtained. The t centers of the radiation source may be fitted based on sine fitting so that t coordinates of the radiation source in the SOT coordinate system may be calculated. The coordinate of the radiation source may be transformed into that of the xOy coordinate system. The t coordinates may be fitted based on line fitting and the center line of the radiation source may be obtained. The circumferential position of the radiation source may be assessed based on the center line.

Merely by way of example, the PET scanner having 96 detector rings. One hundred ninety-one sinograms may be generated. The 191 sinograms may be divided into 6 groups, and each group may have 32 sinograms, except that the last group may have 31 sinograms. Six accumulated sinograms may be generated by fitting the 6 groups of sinograms based on Gaussian fitting. The centers of the radiation source at every angle of the accumulated sinograms may be fitted based on sine fitting, calibrated based on geometry curve correction, and 6 centers may be generated. The 6 centers may be fitted based on line fitting and the center line of the radiation source may be obtained.

In step 2013, the circumferential position of the radiation source may be assessed based on the target circumferential position. If the assessment in step 2013 validates, step 2017 may be performed and the adjustment of the radiation source may be terminated. If the assessment in step 2013 fails, step 2015 may be performed and the table of the PET scanner may be adjusted based on the target circumferential position.

Figure 22A:
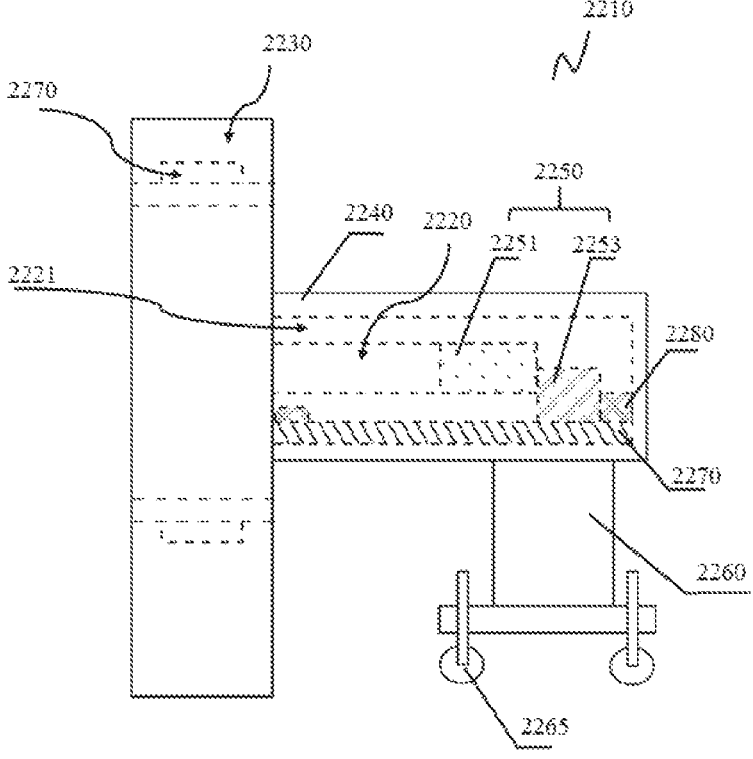
FIG. 22A and FIG. 22B illustrate side view of an exemplary transport device according to some embodiments of the present disclosure.
Figure 22B:
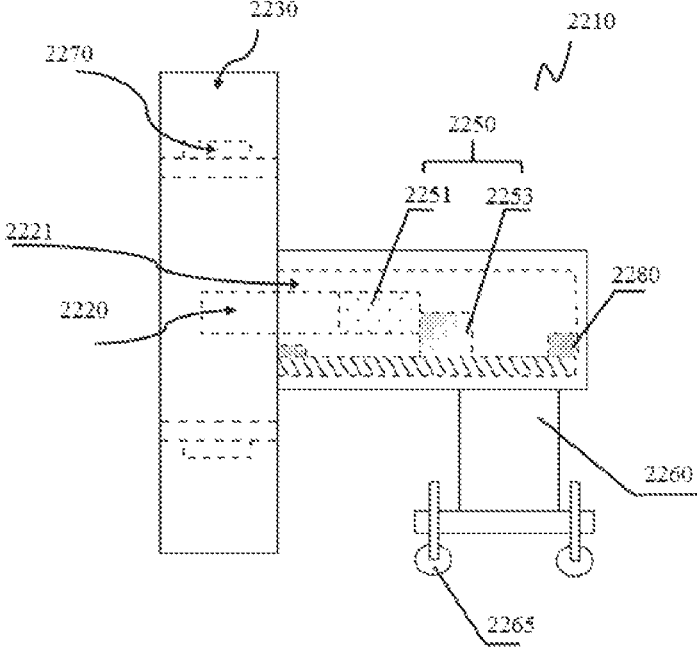

FIG. 22A and FIG. 22B illustrate the side view of an exemplary transport device 2210 according to some embodiments of the present disclosure. The transport device 2210 may include a shield 2240, an adjusting component 2250 that is placed inside the shield 2240, and a base 2260 connected the shield 2240.

The shield 2240 may include an opening 2221. The adjusting component 2250 may be controlled to adjust a radiation source 2220 in the shield 2240. In some embodiments, the adjusting component 2250 may be configured to control the horizontal movement of the radiation source 2220, for example, moving away from the opening 2221, moving close to the opening 2221, etc.

In some embodiments, the shield 2240 may be placed on the base 2260, connected and fixed with the base 2260. In some embodiments, the transport device 2210 may be used to calibrate the PET scanner. Through moving the base 2260 to adjust the position of the transport device 2210, to move the radiation source 2220 to a target position. The shield 2240 may reduce the amount of the radiation emission.

In some embodiments, the adjusting component 2250 may include a fixed component 2251 and a pushing component 2253. The pushing component 2253 may be connected to the fixed component 2251. The pushing component 2253 may be configured to adjust the position of the radiation source 2220 fixed on the fixed component 2251.

As illustrated in FIG. 22A and FIG. 22B, moving the radiation source 2220 to the onset station. Referring to FIG. 22B, the radiation source 2220 may be partially moved in a PET scanner 2230 by the transport device 2210. Annihilation events may occur in the portion of the radiation source 2220 located in the PET scanner 2230, and photons may be generated. The crystal elements of the PET scanner 2230 may be configured to receive the photons and calculate TOF of the photons. Afterwards, the radiation source 2220 may be moved back into the transport device 2210.

In some embodiments, the pushing component 2253 may include a slider and a driving component, the slider may be driven by the driving component to control the movement of the radiation source fixed on the fixed component 2251.

In some embodiments, the sidewall of the shield 2240 may be of a regular shape and have center lines drawn therein. The laser lamp on the left top and the right top of the PET scanner to position the radiation source 2220. In some embodiments, the laser may be aligned with the center lines of the sidewalls of the shield 2240.

In some embodiments, a lead rail 2270 may be mounted in the inner wall of the shield 2240. The lead rail 2270 may stretch across the shield 2240 horizontally from the right to the opening 2221. The lead rail 2270 may be used to reduce the friction between the pushing component 2253 and the inner wall of the shield 2240. The radiation source 2220 may be moved along the lead rail 2270 by the adjusting component 2250. For example, the radiation source 2220 may be moved out of the shield 2240, moved back in the shield 2240, etc.

In some embodiments, at least two limit parts 2280 may be mounted on the lead rail 2270. In some embodiments, the limit part 2280 may include a mechanical limit switch. The pushing component 2250 may be either automatically or manually moved.

In some embodiments, at least the limit part 2280 may include an electrical limit switch, the electrical limit switch may be used to stop the movement of the pushing component 2150 when the pushing component arrives at a target position.

In some embodiments, the base 2260 may include a mobile component 2265. In some embodiments, the mobile component 2265 may include wheels as illustrated in FIG. 22A and FIG. 22B. In some embodiments, the mobile component 2265 may include meshing gears that may be meshed with a moving rail placed on the ground. The moving rail may be used to move the transport device 2210.

Figure 23A:
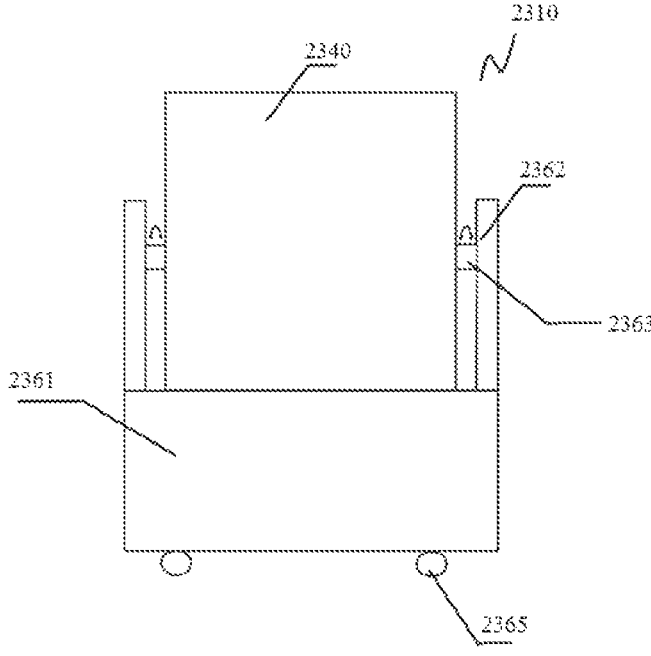
FIG. 23A and FIG. 23B illustrate an exemplary transport device according to some embodiments of the present disclosure.
Figure 23B:
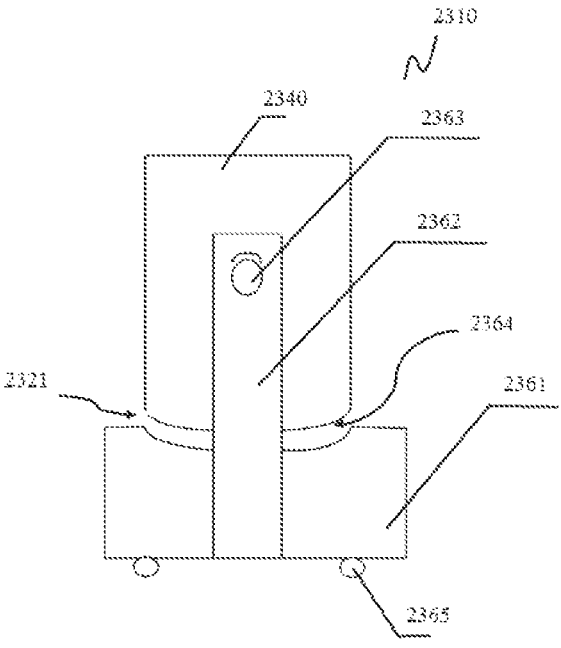

FIG. 23A shows the front view of the transport device 2310 according to some embodiments of the present disclosure. FIG. 23B shows the side view of the transport device 2310 according to some embodiments of the present disclosure.

In some embodiments, the shield 2340 may be connected to the base 2361 through a rotating component 2363. The rotating component 2363 may be used to rotate the shield 2340. In some embodiments, the base 2361 may include a support and two grasp arms 2362 that may be connected to the shield 2340 via the rotating component 2363 located in the two opposite side of the support. In some embodiments, a groove 2364 may be set on the based 2361. The groove 2364 may be used to match the opening 2321 of the shield 2340. In some embodiments, the opening 2321 of the shield 2430 may be an arc as illustrated in the figure.

When a radiation source is move by the transport device 2310, the rotating component 2363 may be rotated either clockwise or counter-clockwise to control the movement of the shield 2340 so that the opening 2321 of the shield 2340 may remain in the groove 2364. As a result, the radiation source may be enclosed in the shield 2340 and may not emit radial rays that may be harmful to an operator of the transport device 2310.

In some embodiments, the base 2361 may include a mobile component 2365. In some embodiments, the mobile component 2365 may include wheels as illustrated in FIG. 23A and FIG. 23B. These embodiments are non-limiting examples, in which represent similar structures to move the transport device 2310 throughout the several views of the drawings. In some embodiments, the mobile component 2365 may include meshing gears that may be meshed with a moving rail placed on the ground. In some embodiments, the mobile component 2365 may include a fiction drive that may be slipped by friction wheels. In some embodiments, the mobile component 2365 may include a chain drive that may drive wheels by a chain. In some embodiments, the mobile component 2365 may include a belt drive that may drive wheels by a belt.

FIG. 24-FIG. 27 illustrate a method for time calibration for the PET scanner. A radiation source 2503 may be placed within the FOV of the PET scanner. The time offset of the PET scanner may be determined based on a first TOF, a second TOF, and the position of the radiation source 2503. The radiation source 2053 may be moveable. A first TOF may be determined based on the coincidence event data for an LOR. The position of the radiation source 2503 may also be determined based on the coincidence event data. A second TOF may be calculated based on the position of the radiation source 2503. The time offset of the PET scanner may be calculated based on the first TOF and the second TOF. In some embodiments, the time offset may be a channel delay.

Figure 25:
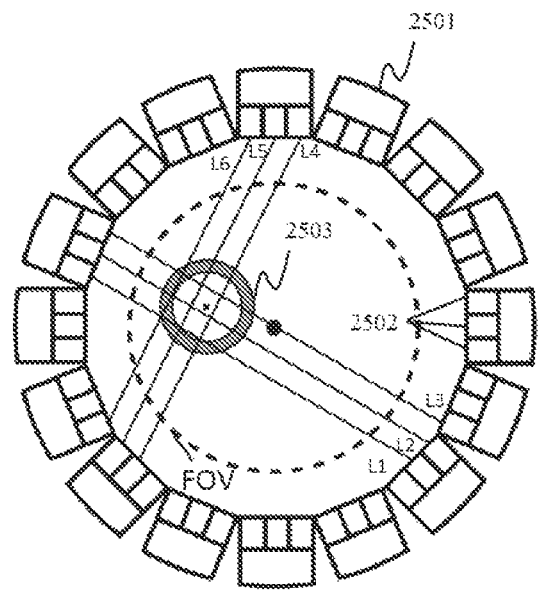
FIG. 25 illustrates an exemplary detector ring according to some embodiments of the present disclosure.

FIG. 25 illustrates an exemplary detector ring of a PET scanner according to some embodiments of the present disclosure. In some embodiments, the PET scanner may include multiple detector rings 2501. A detector ring may include multiple detector units 2502. A radiation source 2503 may be placed inside the FOV of the PET scanner.

FIG. 26 is a flowchart illustrating a process for time calibration for the PET scanner according to some embodiments of the present disclosure. In step 2601, a radiation source may be placed within the FOV of the PET scanner. The radiation source may be used to generate coincidence events. A coincidence event of the coincidence events may produce two photons. The two photons may travel along a same line but at opposite directions. The track of the two photons may be termed as an LOR. Each coincidence event may correspond to a line of response. In some embodiments, the radiation source may be a hollow cylindrical radiation source, a solid cylindrical radiation source, a linear radiation source, etc. In some embodiments, the radiation source may be symmetric. In some embodiments, the radiation source may be asymmetric. In some embodiments, the thickness of the portion of the phantom filled with the radiation source may be uniform. In some embodiments, the thickness of the portion of the phantom filled with the radiation source may be nonuniform. In some embodiments, the size of the radiation source may be determined based on the size of the FOV of the PET scanner. In some embodiments, the diameter of the radiation source may range from $D_{FOV}/2$ to $D_{FOV}$, where $D_{FOV}$ may denote the length of the FOV in the radial direction. In some embodiments, the length of the radiation source in the axial direction may be equal to or more than the length of the FOV in the axial direction. The radiation source may be placed in any suitable position in the PET scanner. In some embodiments, the central axis of the radiation source may be parallel to the central axis of the FOV. In some embodiments, the central axis of the radiation source may be nonparallel to the central axis of the FOV. In some embodiments, the radiation source may be placed at the center of the FOV. In some embodiments, the radiation source may be placed at the peripheral part of the center of the FOV.

In step 2603, TOFs of the LORs may be calculated. In some embodiments, two detector units may be selected in one detector ring 2501 to form a detector unit pair. LOR is the line connecting the two detector units 2502, and the LOR may pass through the radiation source 2503. A plurality of LORs may be determined for the PET scanner. L1, L2, L3, L4, L5, L6 may be exemplary LORs for the PET scanner as illustrated in FIG. 25.

In some embodiments, a table may be used to record the coincidence event data. In some embodiments, an LOR ($r_a$, $r_b$, $i_a$, $i_b$) may denote a coincidence event in the table, where $r_a$ and $r_b$ may denote the axial position of the detector unit pair, $i_a$ and $i_b$ may denote the circumferential position of the detector unit pair, and $i_a<i_b$. The total number of LORs may be calculated by:

$$R_T^2 \frac{I_T(I_T-1)}{2},$$ (Equation 12)

in which $R_T$ may denote the total number of the detector rings in the PET scanner, and $I_T$ may denote the total number of the detector units in a detector ring of the PET scanner.

Figure 27:
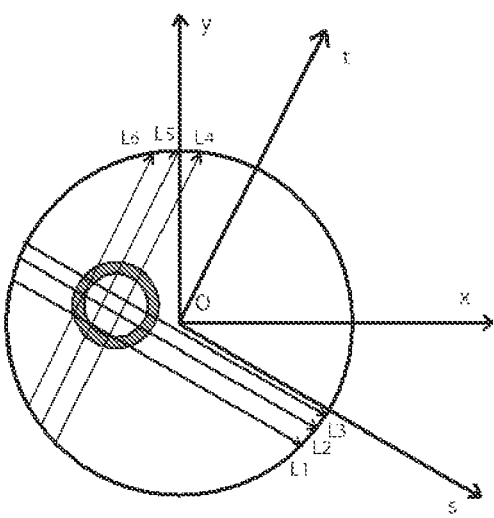
FIG. 27 illustrates an exemplary coordinate system according to some embodiments of the present disclosure.

In some embodiments, a first coordinate system (x-y) may be set up for the detector ring as shown in FIG. 27. The plane determined by the x-axis and the y-axis of the first coordinate system may be parallel to the cross-section of the PET scanner, parallel to the detector ring. A second coordinate system (S-T) may be set up for each LOR in the xOy plane. In some embodiments, the horizontal axis of the second coordinate system may be parallel to the LOR. As shown in FIG. 13, the included angle between the first coordinate system (x-y) and the second coordinate system (S-T) may be Φ. In some embodiments, LOR ($r_a$, $r_b$, $\alpha$, rad) may denote a coincidence event in a sinogram, where $r_a$ and $r_b$ may denote the axial position of the detector unit pair, $\alpha$ may denote the included angle between an LOR and the y-axis of the first coordinate system (x-y), and rad may denote the distance between the LOR and the center of the detector ring (O as shown in FIG. 27).

In some embodiment, an LOR may include a plurality of coincidence events, and each coincidence event may have a TOF. Therefore, the first TOF of the LOR may be an average of all the TOFs of the coincidence events. In some embodiments, the first TOF of the LOR may be the time value at the center of the histogram determined based on all coincidence events occurred on the LOR.

In some embodiments, the first TOF of an LOR may be acquired based on the histogram created based on all coincidence events occurred on the LOR. The time value of the center of the histogram may be that of the first TOF. In some embodiments, the first TOF may be calculated by:

$$\delta t' = \frac{\sum_i \delta t_i n_i}{\sum_i n_i}$$ (Equation 13)

in which i may denote the index number of bin of the histogram, i=−(N−1)/2, −(N−1)/2+1, . . . , 0, 1, 2, . . . , (N−1)/2, N may denote the number of bins, $\delta t_i$ may denote the first TOF of the $i^{th}$ bin, and $n_i$ may denote the number of coincidence events of the $i^{th}$ bin. In some embodiments, N may be an odd number.

In step 2605, the position of the radiation source may be determined and a second TOF of the coincidence event may be calculated based on the position. In some embodiments, the position of the radiation source may be determined based on the reconstructed image of the radiation source.

In some embodiments, the relationship between the x-y coordinate and the S-T coordinate may be calculated by:

$$t = y\cos\varphi - x\sin\varphi,$$ (Equation 14)

in which (x, y) may denote the position of the radiation source in the x-y coordinate system, and (t, φ) may denote the position of the radiation source in the S-T coordinate system.

In some embodiments, the coordinate (x, y) of the radiation source 2503 may be calculated after the coordinate (s, t) is determined.

Figure 24:
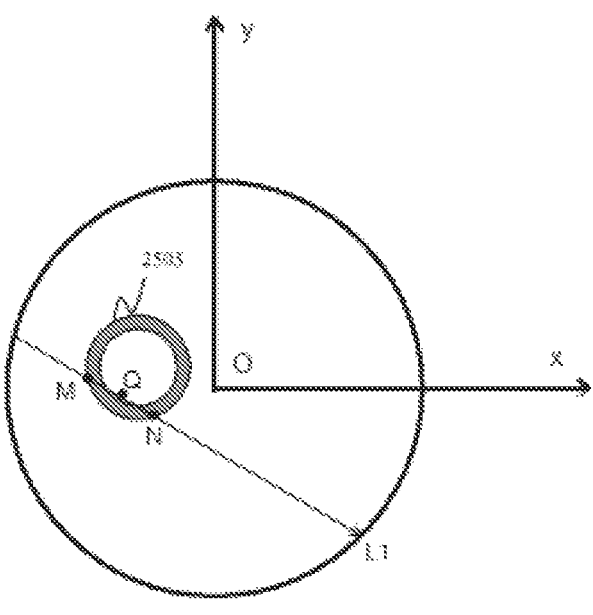
FIG. 24 illustrates an intersection of a radiation source and an LOR according to some embodiments of the present disclosure.

In some embodiments, the second TOF may be determined based on the center of the intersection part between the LOR and the radiation source 2503. As shown in FIG. 24, the LOR L1 may pass through the radiation source 2503. Line segment MN may denote the interaction part between the LOR and the radiation source. Q may denote the center of the line segment MN. The TOF of the coincidence event happening at Q may be determined as the second TOF for L1.

In some embodiments, the distance difference between the travel lengths of the two photons generated in a coincidence event at Q may be denoted as δl. δl may be calculated by:

$$\delta l = 2(y\cos\varphi - x\sin\varphi),$$ (Equation 15)

in which ($x_Q$, $y_Q$) may denote the coordinate of Q in the first coordinate system (x-y), φ may denote the including angle between L1 and the y-axis of the first coordinate system (X-Y).

The TOF of the two photons generated in a coincidence event at Q may be designated as the second TOF δt. δt may be calculated by:

$$\delta t = \delta l / c,$$ (Equation 16)

in which c may denote the speed of light.

In step 2607, the time offset of the detector units on both ends of each LOR may be determined based on the first TOF and the second TOF of the coincidence event for each of a plurality of LORs. In some embodiments, the time offset may be a channel delay of the detector units. In some embodiments, the first TOF for an LOR may be denoted as δt'. The second TOF for an LOR may be denoted as δt. The difference between δt' and δt may be denoted as $\Delta_t$. $\Delta_t$ may be calculated by:

$$\Delta_t = \delta t' - \delta t = TO_a - TO_b.$$ (Equation 17)

in which $TO_a$ and $TO_b$ may denote the channel delay of the two detector units.

In some embodiments, an equation set for the channel delay may be set up. In some embodiments, the channel delay may be calculated by:

$$HT = \Delta t,$$ (Equation 18)

27 -continued 28

$$H = \begin{bmatrix} 1 & -1 & 0 & 0 & \dots \\ 0 & 1 & -1 & 0 & \dots \\ 0 & 0 & 1 & -1 & \dots \\ & \dots & \dots & & \end{bmatrix},$$ (Equation 19)

$$T = \begin{pmatrix} TO_1 \\ TO_2 \\ TO_3 \end{pmatrix},$$ (Equation 20)

and $$\Delta t = \begin{pmatrix} \delta t'_1 - \delta t_1 \\ \delta t'_2 - \delta t_2 \\ \delta t'_3 - \delta t_3 \\ \dots \end{pmatrix},$$ (Equation 21)

in which H may denote a matrix of coefficients, T may denote the channel delay of the two detector units at both ends of the LOR, and $\Delta_t$ may denote the difference between the first TOF $\delta t'$ and the second TOF $\delta t$.

In some embodiments, the channel delay may be obtained through an iteration process for the two detector units at both ends of the LOR. The iteration process may be terminated based on a criteria. In some embodiments, the iterative process may terminated based on the number of iterations. In some embodiments, the iterative process may terminated when the channel delay is less than a threshold.

The relative location of the first detector unit and the corresponding second detector unit is determined based on the dimension of the imaged reconstructed by the PET scanner. For a two-dimensional image reconstruction, the first detector unit and the second detector units may be located in a same detector ring. For a three-dimensional image reconstruction, the first detector unit and the second detector units may not be located in a same detector ring.

In step 2609, the detector unit may be calibrated based on the channel delay calculated in step 2607. In some embodiments, the raw data acquired by the detector unit in practical use may be corrected based on the channel delay. In some embodiments, the channel delay calculated in step 2607 may be stored in the storage of the PET scanner. In some embodiments, the raw data acquired in practical use may be stored. And the channel delay may be used in the image reconstruction process.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for calibrating a PET scanner, the PET scanner having a plurality of detector rings, each detector ring having a plurality of detector units, the method comprising:
    determining a line of response (LOR) connecting a first detector unit and a second detector unit of the PET scanner, wherein the LOR correlates to a plurality of coincidence events resulting from annihilation of positrons emitted by a hollow phantom placed at a position in a field of view (FOV) of the PET scanner, each of the plurality of coincidence events is detected by the first detector unit and the second detector unit, and each of the plurality of coincidence events has a time of flight (TOF);
    determining, based on a relationship between the TOFs and coincidence event counts relating to the TOFs, an offset value associated with the first detector unit; and
    calibrating, based on the offset value, the PET scanner.

2. The method of claim 1, wherein the hollow phantom is a hollow cylindrical phantom.

3. The method of claim 1, comprising:
    creating, based on the TOFs, a histogram representing the relationship between the TOFs and coincidence event counts relating to the TOFs.

4. The method of claim 3, wherein the histogram has at least two peaks.

5. The method of claim 4, wherein the determining, based on a relationship between the TOFs and coincidence event counts relating to the TOFs, an offset value associated with the first detector unit comprising:
    calculating a mean value of time values of the at least two peaks of the histogram.

6. The method of claim 3, wherein the determining, based on a relationship between the TOFs and coincidence event counts relating to the TOFs, an offset value associated with the first detector unit comprising:
    designating a time value of a center of the histogram as the offset value.

7. The method of claim 1, wherein a center axis of the hollow phantom and a center axis of the plurality of detector rings coincide.

8. The method of claim 1, wherein the hollow phantom is placed at a distance from a center axis of the plurality of detector rings.

9. The method of claim 1, wherein the TOF of one of the plurality of coincidence events is determined by:
    determining a first arrival time of a first photon that strikes the first detector unit;
    determining a second arrival time of a second photon that strikes the second detector unit;
    determining, from a time offset table, a time offset associated with the first detector unit and the second detector unit; and
    determining, based on the first arrival time, the second arrival time, and the time offset, the TOF of one of the plurality of coincidence events.

10. A method for calibrating a PET scanner, the PET scanner having a plurality of detector rings, each detector ring having a plurality of detector units, the method comprising:
    determining a line of response (LOR) connecting a first detector unit and a second detector unit of the PET scanner, wherein the LOR correlates to a plurality of coincidence events resulting from annihilation of positrons emitted by a radiation source placed at a position in a field of view (FOV) of the PET scanner, each of the plurality of coincidence events is detected by the first detector unit and the second detector unit, and each of the plurality of coincidence events has a time of flight (TOF);
    creating, based on the TOFs, a histogram having at least two peaks and representing a relationship between the TOFs and coincidence event counts relating to the TOFs;

determining, based on the histogram, an offset value associated with the first detector unit; and calibrating, based on the offset value, the PET scanner.

11. The method of claim 10, wherein the radiation source is accommodated in a hollow phantom.

12. The method of claim 11, wherein the hollow phantom is a hollow cylindrical phantom.

13. The method of claim 11, wherein a center axis of the hollow phantom and a center axis of the plurality of detector rings coincide.

14. The method of claim 11, wherein the hollow phantom is placed at a distance from a center axis of the plurality of detector rings.

15. The method of claim 10, wherein the determining, based on the histogram, an offset value associated with the first detector unit comprising:

calculating a mean value of time values of the at least two peaks of the histogram.

16. The method of claim 10, wherein the determining, based on the histogram, an offset value associated with the first detector unit comprising:

designating a time value of a center of the histogram as the offset value.

17. The method of claim 10, wherein the TOF of one of the plurality of coincidence events is determined by:

determining a first arrival time of a first photon that strikes the first detector unit;

determining a second arrival time of a second photon that strikes the second detector unit;

determining, from a time offset table, a time offset associated with the first detector unit and the second detector unit; and determining, based on the first arrival time, the second arrival time, and the time offset, the TOF of one of the plurality of coincidence events.

18. A positron emission tomography (PET) system having a plurality of detector rings, and each detector ring having a plurality of detector units, the PET system comprising:

a PET scanner;

a coincidence event detection circuit for detecting coincidence events resulting from annihilation of positrons emitted by a hollow phantom placed at a position in a field of view (FOV) of the PET scanner; and a host computer that is configured to perform operations comprising:

determining a line of response (LOR) connecting a first detector unit and a second detector unit of the PET scanner, wherein the LOR correlates to a plurality of coincidence events, each of the plurality of coincidence events is detected by the first detector unit and the second detector unit, and each of the plurality of coincidence events has a time of flight (TOF);

determining, based on a relationship between the TOFs and coincidence event counts relating to the TOFs, an offset value associated with the first detector unit; and calibrating, based on the offset value, the PET scanner.

19. The PET system of claim 18, wherein the hollow phantom is a hollow cylindrical phantom.

20. The PET system of claim 19, wherein the host computer is configured to perform operations comprising:

creating, based on the TOFs, a histogram representing the relationship between the TOFs and coincidence event counts relating to the TOFs.

* * * * *